US007435871B2

(12) United States Patent  
Green et al.

(10) Patent No.: US 7,435,871 B2
(45) Date of Patent: Oct. 14, 2008

(54) TRANSGENIC ANIMALS BEARING HUMAN IGλ LIGHT CHAIN GENES

(75) Inventors: Larry L. Green, San Francisco, CA (US); Vladimir Ivanov, Fremont, CA (US)

(73) Assignee: Amgen Fremont Inc., Fremont, CA (US)

( * ) Notice: Subject to any disclaimer, the term of this patent is extended or adjusted under 35 U.S.C. 154(b) by 340 days.

(21) Appl. No.: 10/307,231

(22) Filed: Nov. 27, 2002

(65) Prior Publication Data

US 2003/0217373 A1 Nov. 20, 2003

Related U.S. Application Data

(60) Provisional application No. 60/334,508, filed on Nov. 30, 2001.

(51) Int. Cl.
*A01K 67/027* (2006.01)
*C12P 21/08* (2006.01)
*C12N 5/06* (2006.01)

(52) U.S. Cl. .................. 800/18; 800/4; 435/70.21; 435/326

(58) Field of Classification Search .......... 800/18, 800/4; 435/70.21, 326
See application file for complete search history.

(56) References Cited

U.S. PATENT DOCUMENTS

| | | | |
|---|---|---|---|
| 5,545,806 A | 8/1996 | Lonberg et al. | 800/2 |
| 5,545,807 A | 8/1996 | Surani et al. | 800/2 |
| 5,569,825 A | 10/1996 | Lonberg et al. | 800/2 |
| 5,625,825 A | 4/1997 | Rostoker et al. | 395/730 |
| 5,661,016 A | 8/1997 | Lonberg et al. | 435/172.3 |
| 5,789,650 A | 8/1998 | Lonberg et al. | 800/2 |
| 5,814,318 A | 9/1998 | Lonberg et al. | 424/184.1 |
| 5,939,598 A | 8/1999 | Kucherlapati et al. | 800/25 |
| 5,994,619 A | 11/1999 | Stice et al. | 800/21 |
| 6,075,181 A | 6/2000 | Kucherlapati et al. | 800/25 |
| 6,114,598 A | 9/2000 | Kucherlapati et al. | 800/18 |
| 6,150,584 A | 11/2000 | Kucherlapati et al. | 800/18 |
| 6,162,963 A | 12/2000 | Kucherlapati et al. | 800/18 |
| 6,300,129 B1 | 10/2001 | Lonberg et al. | 435/326 |
| 6,998,514 B2 * | 2/2006 | Bruggemann | 800/18 |
| 7,074,983 B2 | 7/2006 | Robl et al. | |

FOREIGN PATENT DOCUMENTS

| | | |
|---|---|---|
| EP | 0 463 151 B1 | 1/1992 |
| EP | 1106061 | 6/2001 |
| GB | 2 344 344 | 6/2000 |
| WO | WO 92/03918 | 3/1992 |
| WO | WO 92/22645 | 12/1992 |
| WO | WO 93/12227 | 6/1993 |
| WO | WO 94/02602 | 2/1994 |
| WO | WO 94/25585 | 11/1994 |
| WO | WO 96/22380 | 7/1996 |
| WO | WO 96/33735 | 10/1996 |
| WO | WO 96/34096 | 10/1996 |
| WO | WO 98/24893 | 6/1998 |
| WO | WO 00/26373 | 5/2000 |
| WO | WO 00/76310 | 12/2000 |

OTHER PUBLICATIONS

Kawasaki et al. (1997) Genome Research, vol. 7, 250-261.*
Popov et al. (1996) Gene, vol. 177, 195-201.*
Butler (1998) Revue Scientifique et Technique Office International Des Epizooties. vol. 17, No. 1, pp. 43-70.*
Campbell et al. (1997) Theriogenology, vol. 47 (1), 63-72.*
Babcook et al., "A novel strategy for generating monoclonal antibodies from single, isolated lymphocytes producing antibodies of defined specificities," *PNAS*, 93:7843-7848 (1996).
Frippiat et al., "Organization of the human immunoglobulin lambda light-chain locus on chromosome 22q11.2," *Human Molecular Genetics*. 4(6):983-991 (1995).
Galfre et al., "Preparation of monoclonal antibodies: strategies and procedures," *Methods in Enzymology*, 73:3-46 (1981).
Green et al., "Regulation of B cell development by variable gene complexity in mice reconstituted with human immunoglobulin yeast artificial chromosomes," *Journal of Experimental Medicine*, 188(3):483-495 (1998).
Griffiths et al., "Human anti-self antibodies with high specificity from phage display libraries," *The EMBO Journal*, 12(2):725-734 (1993).
Griffiths et al., "Isolation of high affiinity human antibodies directly from large synthetic repertoires," *The EMBO Journal*, 13(14):3245-3260 (1994).
Gross-Bellard et al., "Isolation of high-molecular-weight DNA from mammalian cells," *European Journal of Biochemistry*, 36:32-38 (1973).
Hermanson et al., "Rescue of end fragments of yeast artifical chromosomes by homologous recombinant in yeast," *Nucleic Acids Research*, 19(18):4943-4948 (1991).
Huxley et al., "Construction of a mouse model of charcot-marie-tooth disease type 1A by pronuclear injection of human YAC DNA," *Human Molecular Genetics*, 5(5):563-569 (1990).
Kawasaki et al., "One-megabase sequence analysis of the human immunoglobulin λ gene locus," *Genome Research*, 7:250-261 (1997).
Mendez et al., "Analysis of the structural integrity of YACs comprising human immunoglobulin genes in yeast and in embryonic stem cells," *Genomics*, 26:294-307 (1995).
Nissim et al., "Antibody fragments from a 'single pot' phage display library as immunochemical reagents," *The EMBO Journal*, 13(3):692-698 (1994).
Pearson, "Empirical statistical estimates for sequence similarity searches," *Journal of Molecular Biology*, 276:71-84 (1998).
Pearson, "Rapid and sensitive sequence comparison with FASTP and FASTA," *Methods in Enzymolology*, 183:63-98 (1990).

(Continued)

*Primary Examiner*—Anne Marie S Wehbe
(74) *Attorney, Agent, or Firm*—Ropes & Gray LLP; Jane T. Gunnison; Raymond M. Doss

(57) ABSTRACT

The invention relates to transgenic animals bearing one or more human λ light chain loci. The invention also relates to methods and compositions for making transgenic animals that have incorporated human λ light chain loci. The invention further relates to methods of using and compositions derived from the transgenic animals that have incorporated human λ light chain loci.

9 Claims, 7 Drawing Sheets

OTHER PUBLICATIONS

Pearson, "Flexible sequence similarity searching with the FASTA3 program package," *Methods in Molecular Biology*, 132:185-219 (2000).

Pearson, "Effective protein sequence comparison," *Methods in Enzymology*, 266:227-258 (1996).

Ray et al., "Generation of a fusion partner to sample the repertoire of splenic B cells destined for apoptosis," *PNAS*, 91:5548-5551 (1994).

Scheistl et al., "High efficiency transformation of intact yeast cells using single stranded nucleic acids as a carrier," *Current Genetics*, 16: 339-346 (1989).

Udey et al., "Human λ light chain locus: Organization and DNA sequences of three genomic J regions," *Immunogenetics*, 25:63-70 (1987).

Williams et al., "Sequence and evolution of the human germline Vλ repertoire," *Journal of Molecular Biology*, 264:220-232 (1996).

T. Duell, et al., "High-Resolution Physical Map of the Immunoglobulin λ Variant Gene Cluster Assembled by Quantative DNA Fiber Mapping," *Genomics*, 45, 479-486 (1997).

I.C. Nicholson, et al., "Antibody Repertoires of Four- and Five-Feature Translocus Mice Carrying Human Immunoglobulin Heavy Chain and κ and λ Light Chain Yeast Artificial Chromosomes," *The Journal of Immunology*, 163, 6898-6906 (1999).

Brüggemann, M., et al., "Strategies for Expressing Human Antibody Repertoires in Transgenic Mice", Immunology Today, vol. 17(8):391-397 (1996).

Brüggemann, M., et al., "Production of Human Antibody Repertoires in Transgenic Mice", Current Opinion in Biotechnology, vol. 8(4):455-458 (1997).

Green, L.L., et al., "Antigen-Specific Human Monoclonal Antibodies from Mice Engineered with Human Ig Heavy and Light Chain YACs", Nature Genetics, vol. 7(1):13-21 (1994).

Ignatovich, O., et al., "Dominance of Intrinsic Genetic Factors in Shaping the Human Immunoglobulin Vλ Repertoire", Journal of Molecular Biology, vol. 294(2):457-465 (1999).

Jakobovits, A., et al., "Germ-line Transmission and Expression of a Human-Derived Yeast Artificial Chromosome", Nature, vol. 362:255-258 (1993).

Jakobovits, A., "Production of Fully Human Antibodies by Transgenic Mice", Current Biology, vol. 6:561-566 (1995).

Mendez, M.J., et al., "Functional Transplant of Megabase Human Immunoglobulin Loci Recapitulates Human Antibody Response in Mice", Nature Genetics, vol. 15(2):146-156, (1997).

Nicholson, I.C., et al., "Antibody Repertoires of Four- and Five-Feature Translocus Mice Carrying Human Immunoglobulin Heavy Chain and κ and λ Light Chain Yeast Artificial Chromosomes", The Journal of Immunology, vol. 163(12):6898-6906 (1999).

Popov, A. V., et al., "A Human Immunoglobulin λ Locus Is Similarly Well Expressed in Mice and Humans", The Journal of Experimental Medicine, vol. 189(10):1611-1619 (1999).

Dunham et al., "The DNA sequence of human chromosome 22," Nature, 402:489-495, (1999).

Green, Larry, "Antibody engineering via genetic engineering of the mouse: Xenomouse strains are a vehicle for the facile generation of therapeutic human monoclonal antibodies," Journal of Immunological Methods, 231(1-2):11-23, (1999).

Kawasaki et al., "Propagation and Maintenance of the 119 Human Immunoglobulin vλ Genes and Pseudogenes During Evolution," Journal of Experimental Zoology, 288:120-134, (2000).

Kellermann et al., "Antibody discovery: the use of transgenic mice to generate human monoclonal antibodies for therapeutics," Pharmaceutical biology, 13(6):593-597, (2002).

Kuroiwa et al., "Manipulation of human minichromosomes to carry greater than megabase-sized chromosome inserts," Nature Biotechnology, 18:1086-1090, (2000).

Mahler et al., "Cloning and expression of human V-genes derived from phage display libraries as fully assembled human anti-TNFχ monoclonal antibodies," Immunotechnology, 3:31-43, (1997).

Nikolaus et al., "A human monoclonal antibody with the capacity to neutralize *Staphylococcus aureus* alpha-toxin," Biosciences Information Service, 1 page, (1994), abstract only.

* cited by examiner

The Human Igλ Locus

FIG. 3    Expression of Human Igλ and Human Igκ in XenoMouse-KL Strains

| Mouse | % CD19+ | % human μ+κ+ in CD19+ | % human μ+λ+ in CD19+ | % κ+ in CD19+ | % human λ+ in CD19+ | % mouse λ+ in CD19+ |
|---|---|---|---|---|---|---|
| wildtype control | 68 | not done | not done | 96 | not done | 4 |
| XMG2 | 75 | 69 | 0 | 69 | 0 | 15 |
| XMG2-KL | 75 | 49 | 41 | 47 | 36 | 8 |
| XMG1 | 65 | 86 | 0 | 85 | 0 | 13 |
| XMG1-KL | 71 | 44 | 31 | 40 | 33 | 9 |

Fusion Summary

| Target Name | Animal # / Strain | # Antigen- | Specific mAbs |
|---|---|---|---|
| MN | 4 each gp | | |
| GP3 | XMG1 | 0 | 0 |
| GP4 | XM3G1-KL | 0 | 1 |
| CEM cells | 4 each gp | anti-CD147 | anti-CD147 |
| GP1 | XMG2 | 5 | 0 |
| GP2 | XMG2-KL | 5 | 3 |
| MCP-1 | 4 each gp | | |
| GP4 | XMG2 | 9 | 0 |
| GP5 | XMG2-KL | 12 | 2 |

Serum Ig Levels in Naive XenoMouse-KL mice

| Mouse ID | yK copy # | Total hκ | Total hλ | Total hIgM | Total IgMκ | Total IgMλ | Total hIgG | Total hIgGκ | Total hIgGλ |
|---|---|---|---|---|---|---|---|---|---|
| F1 129xB6 | N.A. | ND | ND | ND | ND | ND | ND | ND | ND |
| XMG2 | homozygous | 521 | ND | 279 | 316 | ND | 776 | 272 | ND |
| XMG2-KL | homozygous | 483 | 1,312 | 517 | 292 | 219 | 967 | 220 | 1,125 |
| XMG1 | homozygous | 133 | ND | 73 | 73 | ND | 24 | 16 | ND |
| XMG1-KL | hemizygous | 129 | 247 | 258 | 83 | 141 | 91 | 41 | 71 |

SEQUENCE LISTING

<160> NUMBER OF SEQ ID NOS: 17

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cggaccgcct catttgttgt cagatcatg                                      29

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggccggccag cagaatacat gttatctt                                       28

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggccatcgga ccgtcgcgaa tcgatggccg gccgc                               35

<210> SEQ ID NO 4
<211> LENGTH: 35
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 4
ggccgcggcc ggccatcgat tcgcgacggt ccgat                                35

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acgcgttgat gagcaaccac aggcct                                          26

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggccggccag tccatcctgg cttccttc                                        28

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggccatagat ctggccggcc tcgcgaatcg atacgcgtgc                           40

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatcgcggcc gcacgcgtat cgattcgcga ggccggccag atctat                    46

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agtcacatca agatcgttat gg                                              22

<210> SEQ ID NO 10
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 10
gcacggaata tgggactact tcg                                             23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
actccacttc aagtaagagt ttg                                             23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggggtatttg tggaattact t                                               21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cccatctgga tttctaagtg a                                               21

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cggaccgcag agtgagccaa gattgta                                         27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggccggcctg tgctgctgga tgctgtt                                         27

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
            oligonucleotide

<400> SEQUENCE: 16
gataagagtc cctccccaca                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggccatgagc tcagtttctc                                               20
```

TRANSGENIC ANIMALS BEARING HUMAN IGλ LIGHT CHAIN GENES

This application claims the benefit of U.S. Provisional Application No. 60/334,508, filed Nov. 30, 2001.

FIELD OF THE INVENTION

The present invention relates to transgenic non-human animals that are engineered to contain human immunoglobulin loci. In particular, animals in accordance with the invention possess human Ig loci that include plural variable $V_H$ and Vλ gene regions, and may include Vκ gene regions. Advantageously, the inclusion of plural variable region genes enhances the diversity of human antibodies produced by the animal. Further, the inclusion of such regions enhances and reconstitutes B-cell development to the animals, such that the animals possess abundant mature B-cells secreting high-affinity antibodies that comprise human Igλ light chains.

BACKGROUND

The ability to clone and reconstruct megabase-sized human loci in YACs and introduce them into the mouse germline provides a powerful approach to elucidating the functional components of very large or crudely mapped loci as well as generating useful models of human disease. Further, the utilization of such technology for substitution of mouse loci with their human equivalents could provide unique insights into the expression and regulation of human gene products during development, their communication with other systems, and their involvement in disease induction and progression.

One application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development.

Further, the strategy of humanizing a mouse humoral immune system would provide an ideal source for production of fully human antibodies, particularly monoclonal antibodies (Mabs)—an important milestone towards fulfilling the promise of antibody therapy in human disease. Fully human antibodies are expected to minimize the immunogenic and allergic responses intrinsic to non-human (e.g., rodent) or non-human-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

The strategy of humanizing a non-human transgenic animal to produce fully human monoclonal antibodies is important also because it avoids problems encountered with other methods of obtaining fully human antibodies and antibodies that have been altered to reduce adverse immunogenic effects, i.e., "humanized" antibodies. Although useful, humanizing techniques have a number of disadvantages, including labor-intensive protocols and potential alterations of specificity and/or affinity of the variable regions for the original epitope, and contamination of the variable region with residual non-human sequences that may result in host rejection. Making efficacious human monoclonal antibodies in vitro also has proven difficult. Moreover, most of the human monoclonal antibodies produced in vitro have been IgM, which is sometimes associated with immune complex formation and enhanced inflammation.

One approach towards the goal of making fully human antibodies in non-human transgenic animals is to engineer strains deficient in endogenous antibody production that produce human antibodies from large inserted fragments of the human Ig loci. Large fragments have the advantage of preserving large variable gene diversity as well as sequences necessary for the proper regulation of antibody production and expression. By exploiting the host machinery for antibody diversification and selection and the lack of immunological tolerance to human proteins, the human antibody repertoire reproduced in these engineered strains includes high affinity antibodies against any antigen of interest, including human antigens. Then, antigen-specific human Mabs with the desired specificity give readily produced and selected using e.g., hybridoma technology.

The success of this general strategy was demonstrated in connection with the generation of XenoMouse® strains. See e.g., Green et al. *Nature Genetics* 7:13-21 (1994). The XenoMouse® strains were engineered with 245 kb and 190 kb-sized germline configuration fragments of a human heavy chain locus and a human κ light chain loci, respectively, that contained core variable and constant region sequences in yeast artificial chromosomes (YACs). Id. The human Ig-containing YACs proved to be compatible with the mouse system for both rearrangement and expression of antibodies. Moreover, the human loci substituted for the inactivated mouse Ig genes as demonstrated by their ability to support B-cell development and to generate an adult-like human repertoire of fully human antibodies.

This approach is further discussed and delineated in U.S. Pat. Nos. 5,939,598, 6,114,598, 6,075,181, 6,162,963, and 6,150,584; and in International Patent Applications WO 96/22380 and WO98/24893. See also European Patent EP 0 463 151 B1, and International Patent Applications WO 94/02602, WO 96/34096, and WO 96/33735. The disclosures of each of the above-cited patents and applications are hereby incorporated by reference in their entirety.

An alternative approach to making fully human antibodies utilizes an Ig "minilocus". In the minilocus approach, an exogenous Ig locus is mimicked through the inclusion of pieces (individual genes) from the exogenous Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806 and 5,625,825, both to Lonberg and Kay, and GenPharm International U.S. patent application Ser. No. 07/574,748, filed Aug. 29, 1990; Ser. No. 07/575,962, filed Aug. 31, 1990; Ser. No. 07/810,279, filed Dec. 17, 1991; Ser. No. 07/853,408, filed Mar. 18, 1992; Ser. No. 07/904,068, filed Jun. 23, 1992; Ser. No. 07/990,860, filed Dec. 16, 1992; Ser. No. 08/053,131, filed Apr. 26, 1993; Ser. No. 08/096,762, filed Jul. 22, 1993; Ser. No. 08/155,301, filed Nov. 18, 1993; Ser. No. 08/161,739, filed Dec. 3, 1993; Ser. No. 08/165,699, filed Dec. 10, 1993; and Ser. No. 08/209,741, filed Mar. 9, 1994; the disclosures of which are hereby incorporated by reference. See also International Patent Applications WO 94/25585, WO 93/12227, WO 92/22645, and WO 92/03918, the disclosures of which are hereby incorporated by reference in their entirety. See further Taylor et al., 1992, Chen et al., 1993, Tuaillon et al., 1993, Choi et al., 1993, Lonberg et al. (1994), Taylor et al. (1994), and Tuaillon et al. (1995), the disclosures of which are hereby incorporated by reference in their entirety.

An advantage of the minilocus approach is the rapidity with which constructs including portions of the Ig locus can be generated and introduced into animals. A significant disadvantage of the minilocus approach, however, is that, in theory, insufficient diversity is introduced through the inclusion of only small numbers of V, D, and J genes. Indeed, the published reports, including U.S. Pat. No. 6,300,129, describe B-cell development and antibody production in animals produced by the minilocus approach that appears stunted.

Accordingly, there is a need for producing non-human transgenic animals that comprise more complete Ig loci than has previously been produced to obtain transgenic animals having a substantially complete human antibody repertoire. Introduction of other Ig loci into a transgenic non-human animal may permit greater antibody diversity and would be likely to reconstitute a more complete immune repertoire of the animals. Thus, it would be desirable to provide transgenic animals stably containing more complete Ig V gene germline sequences, particularly having germline Vλ sequences. It would be additionally desirable to provide such loci against a knockout background of endogenous Ig. Animals capable of producing such a repertoire can be used to create immortalized cells, such as hybridomas, that make fully human monoclonal antibodies for both diagnostic and therapeutic purposes.

SUMMARY OF THE INVENTION

The invention provides non-human transgenic animals bearing a substantially complete human immunoglobulin (Ig) λ locus. The human λ locus comprises greater than 60%, preferably greater than 70% or 80%, more preferably greater than about 90% or 95%, and even more preferably 100% or about 100% of the human λ light chain variable region genes. Such percentages preferably refer to percentages of functional variable region genes in preferred embodiments, the animal is a mammal.

In another embodiment, the transgenic animals further comprise human Ig heavy and κ light chain loci. Preferably, the heavy chain locus includes greater than about 20%, more preferably greater than about 40%, more preferably greater than about 50%, and even more preferably greater than about 60% of the human heavy chain variable region. Most preferably, the heavy chain locus comprises greater than about 70%, 80%, 90% or 95% of the human heavy chain variable region, or comprises 100% or substantially 100% of the human heavy chain variable region genes. With respect to the human κ light chain, the locus preferably includes greater than about 20%, more preferably greater than about 40%, more preferably greater than about 50%, and even more preferably greater than about 60% of the human κ light chain variable region genes. Most preferably, the human κ chain locus comprises greater than about 70%, 80%, 90% or 95% of the human κ chain variable region, or comprises 100% or substantially 100% of the human κ chain variable region.

Further, such animals preferably include the entire $D_H$ region, the entire $J_H$ region and the human mu constant region, and can additionally be equipped with genes encoding other human constant regions for the generation of additional isotypes. Such isotypes can include genes encoding $\gamma_1, \gamma_2, \gamma_3, \gamma_4$, α and ε encoding genes. Additional constant regions can be included on the same transgene, i.e., downstream from the human mu constant region, or, alternatively, such other constant regions can be included on another chromosome. It will be appreciated that where such other constant regions are included on the same chromosome as the chromosome including the human mu constant region encoding transgene, cis-switching to the other isotype or isotypes can be accomplished. On the other hand, where such other constant region is included on a different chromosome from the chromosome containing the mu constant region encoding transgene, trans-switching to the other isotype or isotypes can be accomplished. Such arrangement allows tremendous flexibility in the design and construction of non-human transgenic animals for the generation of antibodies to a wide array of antigens.

In certain embodiments, the non-human transgenic animal additionally does not produce functional endogenous immunoglobulins. This may be accomplished by inactivating (e.g., knocking out) the endogenous heavy and λ and κ light chain Ig loci using methods known in the art or described herein. For example, the endogenous genes may be inactivated through utilization of homologous recombination vectors that replace or delete the region. Such techniques are described in detail U.S. Pat. Nos. 5,939,598, 6,114,598, 6,075,181, 6,162, 963, and 6,150,584, in WO 98/24893, and in publications such as Green et al. *Nature Genetics* 7:13-21 (1994). In a preferred embodiment, the transgenic animals are mice, including mice of the XenoMouse® line.

In another embodiment, the non-human transgenic animal comprises substantially inactive endogenous heavy chain and κ light chain loci but comprises an active endogenous λ light chain locus. Applicants have found that endogenous expression of the λ light chain in transgenic mice is sufficiently low that it does not interfere with production of antibodies comprising a human λ light chain.

In preferred embodiments, the transgenic non-human mammal having a modified genome, wherein the genome modifications comprise at least one inactivated endogenous immunoglobulin locus, such that the mammal would not display normal B-cell development; an inserted human λ light chain Ig locus in substantially germline configuration, the human λ light chain Ig locus comprising a human λ constant region, a plurality of Jλ genes and a plurality of Vλ genes; an inserted human heavy chain Ig locus in substantially germline configuration, the human heavy chain Ig locus comprising a human μ constant region and regulatory and switch sequences thereto, a plurality of human $J_H$ genes, a plurality of human $D_H$ genes, and a plurality of human $V_H$ genes; and an inserted human κ light chain Ig locus in substantially germline configuration, the human κ light chain Ig locus comprising a human κ constant region, a plurality of Jκ genes and a plurality of Vκ genes; wherein the number of Vλ, $V_H$ and Vκ genes inserted are sufficient to substantially restore normal B-cell development in the mammal.

In a preferred embodiment, the heavy chain Ig locus comprises a second constant region selected from the group consisting of all subtypes of human gamma, alpha, delta, and epsilon. Where present, the number of $V_H$ genes is preferably greater than about 20. In another preferred embodiment, the number of Vκ genes is greater than about 15. In a preferred embodiment, the number of $D_H$ genes is greater than about 20, the number of $J_H$ genes is greater than about 4, the number of $V_H$ genes is greater than about 20, the number of Jκ genes is greater than about 4, the number of Vκ genes is greater than about 15 and the number of Vλ genes is greater than about 15, more preferably greater than about 20 or about 25, and even more preferably is about 30. In another embodiment, the number of functional Jλ-Cλ pairs is four.

In another preferred embodiment, the number of $D_H$ genes, the number of $J_H$ genes, the number of $V_H$ genes, the number of Jκ genes, the number of Vκ genes, the number of Jλ genes and the number of Vλ genes are selected such that the Ig loci are capable of encoding greater than about $1 \times 10^5$ different functional antibody sequence combinations in a population of transgenic animals. In a preferred embodiment, B-cell development in a population is reconstituted on average to greater than about 50% compared to wild type, more preferably greater than 60%, 70%, 80%, 90% or 95% as compared to wildtype.

In accordance with another aspect, the present invention provides a transgenic non-human mammal having a modified genome that render the mammal capable of producing human immunoglobulin molecules but substantially incapable of producing functional endogenous immunoglobulin molecules, wherein the genome of the mammal comprises sufficient human $V\lambda$, $J\lambda$-$C\lambda$ pairs, $V_H$, $D_H$, $J_H$, $V\kappa$, and $J\kappa$ genes to encode an antibody repertoire of at least about $1 \times 10^6$ different functional human immunoglobulin sequence combinations. In a preferred embodiment, the number of human $V\lambda$, $V_H$ and $V\kappa$ genes is sufficient to substantially restore normal B-cell development in the mammal. In a preferred embodiment, B-cell development in a population of mammals is reconstituted on average to greater than about 50% as compared to wild type, more preferably greater than 60%, 70%, 80%, 90% or 95% as compared to wildtype.

In another aspect, the invention provides a transgenic non-human mammal having a modified genome comprising an inactivated endogenous heavy chain immunoglobulin) locus; an inserted human heavy chain Ig locus comprising substantially all of the human heavy chain locus or comprising a nucleic acid sequence substantially corresponding to the nucleic acid sequence of a human heavy chain locus; an inserted human κ light chain Ig locus comprising substantially all of the κ light chain Ig locus or a nucleic sequence substantially corresponding to the nucleic acid sequence of the κ light chain Ig locus; and an inserted human λ light chain Ig locus comprising substantially all of the λ light chain Ig locus or a comprising nucleic acid sequence substantially corresponding to the nucleic acid sequence of yL. In a further aspect, the transgenic non-human mammal may further comprise inactivated endogenous κ and/or λ light chain Ig loci.

The invention further provides a transgenic non-human mammal having a modified genome comprising an inactivated endogenous heavy chain immunoglobulin locus; an inserted human heavy chain Ig locus comprising a nucleic acid sequence substantially corresponding to all of the human heavy chain locus but lacking the human γ2 constant region; an inserted human κ light chain Ig locus comprising a nucleic acid sequence substantially corresponding to the nucleic acid sequence of the κ light chain Ig locus; and an inserted human λ light chain Ig locus comprising substantially all of the λ light chain Ig locus or comprising a nucleic acid sequence substantially corresponding to the nucleic acid sequence of the λ light chain Ig locus. In a further aspect, the transgenic non-human mammal may further comprise inactivated endogenous κ and/or λ light chain Ig loci.

In another aspect, the invention provides a method for producing transgenic non-human animal having a modified genome, wherein the method comprises introducing a human λ light chain Ig locus or portion thereof into a cell, and optionally introducing a human heavy chain Ig locus and/or human κ light chain Ig locus into the cell, and manipulating the cell to produce a transgenic non-human animal. In a preferred embodiment, the immunoglobulin locus is introduced using a yeast artificial chromosome (YAC) comprising the human immunoglobulin locus. The invention also provides transgenic mice and transgenic offspring therefrom produced via this method.

In accordance with another aspect, the present invention provides a transgenic animal having a modified genome comprising an inserted human heavy chain Ig transgene, an inserted human λ light chain Ig transgene and an inserted human κ light chain Ig transgene, wherein the transgenes comprise selected sets of human variable region genes that enable human-like junctional diversity and human-like complementarity determining region 3 (CDR3) lengths. In a preferred embodiment, the human-like junctional diversity of the heavy chain comprises average N-addition lengths of 7.7 bases. In another preferred embodiment, the human-like heavy chain CDR3 lengths comprise between about 2 through about 25 residues with an average of about 14 residues.

The invention also provides a method for making immortalized cell lines and the human antibodies produced thereby comprising immunizing a non-human transgenic animal of the invention with an antigen; collecting and immortalizing lymphocytic cells to obtain an immortalized cell population; identifying and isolating specific cell populations secrete human antibodies that specifically bind to the antigen with an affinity of greater than $10^9$ $M^{-1}$; and isolating the antibodies from the cell populations.

The invention also provides polyclonal antibodies comprising human λ light chain molecules derived from the non-human transgenic animals of the invention. In a preferred embodiment, the polyclonal antibodies further comprise a human heavy chain.

The invention also provides nucleic acid molecules comprising a full-length human λ light chain Ig locus. The invention also provides nucleic acid molecules encoding human λ light chains from antibodies produced by the transgenic animals or cells of the invention.

Particularly preferred embodiments of the invention are provided in the following numbered paragraphs:

1. A transgenic animal comprising a substantially complete human λ light chain locus comprising V, J, and constant region genes.

2. A transgenic animal comprising a portion of a human λ light chain locus, wherein said portion comprises at least 500 kb of said locus.

3. The transgenic animal of paragraphs 1 or 2, wherein said animal is heterozygous or homozygous for a substantially inactivated endogenous immunoglobulin heavy chain locus.

4. The transgenic animal of paragraphs 1 or 2, wherein said animal is heterozygous or homozygous for a substantially inactivated endogenous immunoglobulin κ light chain locus.

5. The transgenic animal of paragraphs 1 or 2, wherein said animal is heterozygous or homozygous for a substantially inactivated endogenous λ immunoglobulin light chain locus.

6. The transgenic animal of any one of paragraphs 1-5, wherein said animal further comprises a human immunoglobulin heavy chain locus comprising V, D, J, and constant region genes or a portion thereof.

7. The transgenic animal of any one of paragraphs 1-6, wherein said animal further comprises a human immunoglobulin κ light chain locus comprising V, J, and constant region genes or a portion thereof.

8. The transgenic animal of any one of paragraphs 1-7, wherein said human λ light chain locus is capable of being expressed by said transgenic animal.

9. The transgenic animal of any one of paragraphs 1-8, wherein said transgenic animal is a mouse, a rat, a dog, a monkey, a goat, a pig, a cow, a hamster, a rabbit, a horse, a sheep, a guinea pig, or a bird.

10. The transgenic animal of any one of paragraphs 1-9, wherein said transgenic animal is a mouse.

11. The transgenic animal of any one of paragraphs 1-10, wherein said transgenic animal targets said human λ light chain locus for VJ recombination.

12. The transgenic animal of paragraph 6, wherein said human immunoglobulin heavy chain locus is capable of being expressed by said transgenic animal.

13. The transgenic animal of paragraph 7, wherein said human κ locus is capable of being expressed by said transgenic animal.

14. The transgenic animal of any one of paragraphs 1-13, wherein said human λ locus is effective for expression.

15. The transgenic animal of any one of paragraphs 3-5, wherein said substantial inactivation of said endogenous locus is a result of introducing a genetic lesion.

16. The transgenic animal of paragraph 15, wherein said genetic lesion is in the J region of said endogenous locus.

17. The transgenic animal of any one of paragraphs 4-5, wherein said substantially inactivated endogenous light chain locus comprises a genetic lesion in the constant region of said endogenous light chain locus.

18. The transgenic animal of paragraph 2, wherein said human λ light chain locus is between 600 kb and 0.9 Mb.

19. The transgenic animal of paragraph 2, wherein said human λ light chain locus is between 700 kb and 0.9 Mb or more and encompasses the complete human Ig λ locus.

20. The transgenic animal of paragraph 2, wherein said human λ light chain locus is between 800 kb and 0.9 Mb or more and encompasses the complete human Ig λ locus.

21. A transgenic animal comprising
   a. a substantially inactivated endogenous heavy chain locus;
   b. a substantially inactivated endogenous κ light chain locus;
   c. a human heavy chain locus comprising V, D, J, and constant region genes;
   d. a human κ light chain locus comprising V, J, and constant region genes; and
   e. a substantially complete human λ light chain locus comprising V, J, and constant region genes.

22. The transgenic animal of paragraph 21, further comprising a reconstituted primary or secondary B lymphocytic population wherein the level of said population is chosen from the group consisting of 5-20% that of a wild type animal, 20-40% that of a wild type animal, 40-60% that of a wild type animal, 60-80% that of a wild type animal, 80-100% that of a wild type animal, and 100-200% that of a wild type animal.

23. A method for producing an antisera comprising a human antibody directed against an antigen from a transgenic animal, comprising:
   a. immunizing the transgenic animal of any one of any one of paragraphs 1-22 with said antigen;
   b. allowing said transgenic animal to mount an immune response to said antigen; and
   c. collecting the serum from said transgenic animal.

24. A method for isolating a human antibody directed against an antigen from a transgenic animal, comprising:
   a. immunizing the transgenic animal of any one of paragraphs 1-22 with said antigen;
   b. allowing said transgenic animal to mount an immune response to said antigen;
   c. collecting the serum from said transgenic animal; and
   d. purifying said transgenic antibody from said serum.

25. An antibody derived from the method of paragraph 24, wherein said antibody has a dissociation constant of less than a value selected from the group consisting of $1\times10^{-7}$ M, $1\times10^{-8}$ M, $1\times10^{-9}$ M, $1\times10^{-10}$ M, $1\times10^{-11}$ M, $1\times10^{-12}$ M and $1\times10^{-13}$ M.

26. A method for producing a cell line that produces a human monoclonal antibody or a fragment thereof directed to an antigen, comprising:
   a. immunizing the transgenic animal of any one of paragraphs 1-22 with said antigen;
   b. allowing said transgenic animal to mount an immune response to said antigen;
   c. isolating B lymphocytes from said transgenic animal;
   d. immortalizing said B lymphocytes;
   e. creating individual monoclonal populations of said immortalized B-lymphocytes; and
   f. screening said immortalized B lymphocytes to identify an antibody directed to said antigen.

27. The method according to paragraph 26, wherein said immortalized cell is derived from a mouse cell, a rat cell, a dog cell, a monkey cell, a goat cell, a pig cell, a cow cell, a hamster cell, a rabbit cell, a horse cell, a sheep cell, a guinea pig cell, or a bird cell.

28. An isolated monoclonal antibody produced by the method of paragraphs 26 or 27.

29. A primary cell or progeny thereof derived from the transgenic animal of any one of paragraphs 1-27.

30. An immortalized cell or progeny thereof derived from the transgenic animal of any one of paragraphs 1-22.

31. The immortalized cell or progeny thereof of paragraphs 29 or 30, wherein said immortalized cell is of B lymphocytic origin.

32. The immortalized cell or progeny thereof of paragraph 31, wherein said immortalized cell is a hybridoma.

33. A transgenic mouse comprising a substantially complete human λ light chain locus comprising V, J, and constant region genes, wherein said transgenic mouse targets said human λ light chain locus for VJ recombination, and wherein said transgenic mouse is capable of expressing said human λ light chain locus.

34. A transgenic mouse comprising a portion of a human λ light chain locus, wherein said portion comprises at least 500 kb of said locus, wherein said transgenic mouse targets said human λ light chain locus for VJ recombination, and wherein said transgenic mouse is capable of expressing said human λ light chain locus.

35. A method for producing a transgenic animal, comprising:
   a. combining under fusing conditions (1) yeast spheroplasts having incorporated a YAC comprising a substantially complete human λ light chain locus or a portion thereof comprising at least 500 kb of said human λ light chain locus and a selectable marker with (2) embryonic stem cells of a host animal, whereby said human λ light chain locus or portion thereof and selectable marker are incorporated into the genome of said embryonic stem cells;
   b. selecting for embryonic stem cells that have incorporated said selectable marker and thereby selecting for cells comprising said human λ light chain locus or portion thereof;
   c. transferring said selected embryonic stem cells into a host blastocyst and implanting said blastocyst in a pseudopregnant animal recipient;
   d. allowing said blastocyst to develop to term to produce a chimeric animal carrying said human λ light chain locus or portion thereof; and
   e. mating said chimeric animal with an animal of the same species to produce said transgenic animal, wherein said transgenic animal has inherited said human λ light chain locus or portion thereof from said chimeric animal.

36. The method according to paragraph 35, wherein said selectable marker is the HPRT gene, the neomycin resistance gene, the hygromycin resistance gene, fl-gal, or GPT.

37. The method of paragraph 35, wherein said embryonic stem cell is deficient in endogenous heavy chain, κ light chain and/or λ light chain expression.

38. The method according to paragraph 35, wherein said step of mating produces a transgenic animal heterozygous for said human λ light chain locus or portion thereof and said heterozygous animal is mated to another transgenic animal heterozygous for said human λ light chain locus to produce a transgenic animal homozygous for said human λ light chain locus.

39. The method of paragraph 35, wherein said YAC comprises a human λ light chain locus of between 600 kb and 0.9 Mb.

40. The method of paragraph 35, wherein said YAC comprises a human λ light chain locus of between 700 kb and 0.9 Mb.

41. The method of paragraph 35, wherein said YAC comprises a human λ light chain locus of between 800 kb and 0.9 Mb.

42. The transgenic animal produced by the method of any one of paragraphs 35-41.

43. The transgenic animal according to claim 42, wherein said transgenic animal is selected from the group consisting a mouse, a rat, a dog, a monkey, a goat, a pig, a cow, a hamster, a rabbit, a horse, a sheep, a guinea pig, and a bird.

44. A non-human embryonic stem cell or progeny thereof, comprising a substantially complete human λ light chain locus or a portion thereof, wherein said portion comprises at least 500 kb of said human λ light chain locus.

45. The non-human embryonic stem cell or progeny thereof of paragraph 44, further comprising a genetic lesion in the J and/or constant regions of one or more of the endogenous immunoglobulin loci of said non-human embryonic stem cell or progeny thereof.

46. The non-human embryonic stem cell or progeny thereof of paragraph 45, wherein said genetic lesion is an insertion of a human immunoglobulin sequence.

47. The non-human embryonic stem cell or progeny thereof of paragraph 45, wherein said genetic lesion resulted from the targeted disruption of one or more of said endogenous immunoglobulin loci by a selectable marker gene.

48. The non-human embryonic stem cell or progeny thereof of paragraph 47, wherein said selectable marker gene is the HPRT gene, the neomycin resistance gene, the hygromycin resistance gene, fl-gal, or GPT.

49. The non-human embryonic stem cell or progeny thereof of paragraph 45, wherein said genetic lesion comprises a deletion of one or more of said endogenous immunoglobulin loci.

50. The non-human embryonic stem cell or progeny thereof of paragraph 46, wherein said stem cell or progeny thereof is homozygous for said genetic lesion.

51. The non-human embryonic stem cell or progeny thereof of paragraph 46, wherein said genetic lesion is in an immunoglobulin heavy chain J region.

52. The non-human embryonic stem cell or progeny thereof of paragraph 46, wherein said genetic lesion comprises replacement of at least a portion of said endogenous immunoglobulin light chain loci with said substantially complete human immunoglobulin-λ light chain locus by homologous recombination.

53. The non-human embryonic stem cell or progeny thereof of paragraph 46, comprising a genetic lesion in both endogenous copies of an immunoglobulin locus of said non-human embryonic stem cell or progeny thereof, wherein said genetic lesion results in the inability of both copies of said immunoglobulin locus to rearrange.

54. A method for producing a transgenic animal, comprising interbreeding a first parent and a second parent, and recovering progeny thereof, wherein said first parent comprises:
  a. a substantially inactivated endogenous heavy chain locus;
  b. a substantially inactivated endogenous κ light chain locus;
  c. a human heavy chain locus comprising V, D, J, and constant region genes; and
  d. a human κ light chain locus comprising V, J, and constant region genes;
wherein said second parent comprises a substantially complete human λ light chain locus comprising V, J, and constant region genes; wherein said progeny comprises:
  a. a substantially inactivated endogenous heavy chain locus;
  b. a substantially inactivated endogenous κ light chain locus;
  c. a human heavy chain locus comprising V, D, J, and constant region genes;
  e. a human κ light chain locus comprising V, J, and constant region genes; and
  f. a substantially complete human λ light chain locus comprising V, J, and constant region genes.

55. The transgenic animal produced by the method of paragraph 54.

56. The transgenic animal produced by the method of paragraph 54, wherein said transgenic animal is a mouse, a rat, a dog, a monkey, a goat, a pig, a cow, a hamster, a rabbit, a horse, a sheep, a guinea pig, or a bird.

57. A nucleic acid molecule isolated from the transgenic animal according to any one of paragraphs 1-22, wherein said isolated nucleic acid molecule encodes a human λ light chain or an antigen-binding portion thereof.

58. The isolated nucleic acid molecule according to paragraph 57, wherein said nucleic acid molecule is isolated from a B lymphocyte or progeny thereof that produces said human λ light chain.

59. The isolated nucleic acid molecule of paragraph 58, wherein said progeny of said B lymphocyte is a hybridoma.

60. The isolated nucleic acid molecule of paragraph 57 wherein said isolated nucleic acid molecule comprises the sequence encoding between one to three of the CDR regions of said human antibody.

61. A vector comprising the nucleic acid molecule, or fragment thereof, according to any one of paragraphs 57-60.

62. The vector according to paragraph 61, wherein said vector further comprises expression control sequences operably linked to said nucleic acid molecule.

63. A nucleic acid molecule isolated from the transgenic animal according to any one of paragraphs 1-22 that encodes a human λ light chain or an antigen-binding portion thereof, wherein said light chain is the light chain of an antibody that specifically binds to an antigen of interest.

64. The isolated nucleic acid molecule of paragraph 63, wherein said nucleic acid molecule is isolated from a B lymphocyte or progeny thereof that produces said human λ light chain or antigen-binding portion thereof.

65. The isolated nucleic acid molecule of paragraph 64, wherein said progeny of said B lymphocyte is a hybridoma.

66. The isolated nucleic acid molecule of paragraph 63 wherein said isolated nucleic acid molecule comprises the sequence encoding between one to three of the CDR regions of said human antibody.

67. A vector comprising the nucleic acid molecule according to any one of paragraphs 63-66.

68. The vector according to paragraph 67, wherein said vector further comprises an expression control sequence operably linked to said nucleic acid.

69. An isolated host cell, comprising
  a) a nucleic acid molecule that was isolated from a transgenic animal according to any one of paragraphs 1-22 that encodes a human λ light chain or an antigen-binding portion thereof, wherein said light chain is the light chain of an antibody that specifically binds to an antigen of interest; or
  b) a vector comprising said nucleic acid molecule.

70. An isolated host cell, comprising:
  a) a nucleic acid molecule that was isolated from a transgenic animal according to any one of paragraphs 1-22 and encodes a human heavy chain or the antigen-binding portion thereof and an isolated nucleic acid molecule that encodes a human λ light chain or the antigen-binding portion thereof, wherein said heavy chain and said light chain form an antibody that specifically binds to an antigen of interest; or
  b) a vector or vectors comprising said nucleic acid molecules.

71. The isolated host cell of either of paragraphs 69 or 70 wherein said cells are chosen from the list consisting of hybridoma cells, bacterial cells, yeast cells, insect cells, amphibian cells and mammalian cells.

72. The host cell according to paragraph 71, wherein said mammalian cell is a mouse cell, a rat cell, a dog cell, a monkey cell, a goat cell, a pig cell, a cow cell, a hamster cell, a rabbit cell, a horse cell, a sheep cell, a guinea pig cell, or a bird cell.

73. The host cell of paragraph 71, wherein said mammalian cells are HeLa cells, NIH 3T3 cells, CHO cells, 293 cells, BHK cells, VERO cells, CV-1 cells, NS/0 cells, or COS cells.

74. A method of recombinantly producing a human immunoglobulin-λ light chain or the antigen-binding portion thereof, or both said human immunoglobulin-λ light chain and a human immunoglobulin heavy chain or antigen-binding portions thereof, that was identified from a transgenic animal and specifically binds to an antigen of interest, comprising the step of cultivating the host cell according to any one of paragraphs 69-73 under conditions in which the nucleic acid molecules are expressed.

75. A non-human transgenic animal, comprising the nucleic acid molecule of paragraph 63, wherein said non-human transgenic animal expresses said nucleic acid molecule.

76. A non-human transgenic animal comprising an isolated nucleic acid molecule that encodes an immunoglobulin heavy chain or the antigen-binding portion thereof and an isolated nucleic acid molecule that encodes an immunoglobulin-λ light chain or the antigen-binding portion thereof of a human antibody that specifically binds to an antigen of interest, wherein said animal expresses said nucleic acid molecules.

77. The non-human transgenic animal according to any one of paragraphs 75-76, wherein said animal is a mouse, a rat, a dog, a monkey, a goat, a pig, a cow, a hamster, a rabbit, a horse, a sheep, a guinea pig, or a bird.

78. The non-human transgenic animal according to any one of paragraphs 75-76, wherein a human antibody resulting from expression of said isolated nucleic acid molecules or a portion thereof is expressed on the surface of cells derived from said animal's B lymphocytic cells or progeny thereof.

79. The non-human transgenic animal according to any one of paragraphs 75-76, wherein a human antibody resulting from expression of said isolated nucleic acid molecules or a portion thereof is secreted into the lymph, blood, milk, saliva, or ascites of said animal.

80. The transgenic animal of any one of claims 1-5, wherein at least 95% of a population of said transgenic animals maintains the human λ light chain locus for at least three generations.

81. The transgenic animal of claim 21, wherein at least 95% of a population of said transgenic animals maintains the human λ light chain locus, human λ light chain locus and human heavy chain locus for at least three generations.

DESCRIPTION OF THE DRAWINGS

FIG. 3 is a chart showing the expression of human Igλ and human Igκ in XenoMouse®-KL strains.

FIG. 4 presents a summary of the fusion experiments described in Example 8.

FIG. 5 is a chart showing serum levels of human antibodies in naive XenoMouse®-KL mice.

DETAILED DESCRIPTION OF THE INVENTION

Figure 1:
FIG. 1 shows the human immunoglobulin λ locus comprising 30 functional Vλ genes, and seven Jλ-Cλ pairs, of which four are functional.

Herein we describe the generation and characterization of several strains of mice comprising a human germline λ Ig light chain locus or a part thereof. We also describe the production of transgenic animals further comprising a human germline κ light chain locus or part thereof and a human germline heavy chain locus or part thereof. Thus, the present invention provides transgenic non-human animals comprising the large and complex human Ig loci to functionally replace the corresponding mouse loci. The invention also provides methods for producing the transgenic non-human animals by using YACs comprising the human λ germline locus and the successful introduction of the megabase-sized YACs into transgenic animals, particularly transgenic mice. The invention also provides embryonic stem cells that give rise to the transgenic animals as well as methods for making the embryonic stem cells. The invention further provides antibodies produced by the transgenic animals, both polyclonal and monoclonal, and provides compositions and methods related to immortalized cells, e.g. hybridomas, that make the monoclonal antibodies.

Definitions

The terms herein generally have their usual meaning as understood by those of ordinary skill in the art. The following terms are intended to have the following general meanings as they are used herein:

"Antibody repertoire" refers to the sum of every different antibody species in an animal or human. Diversity in antibody repertoires results from, inter alia, immunoglobulin gene recombination, immunoglobulin gene junctional diversity, terminal deoxynucleotide transferase activity, exonuclease activity, receptor editing, and somatic hypermutation.

"B lymphocytic cells or progeny thereof" refer to any cell descending from, or destined for, the B lymphocytic lineage. Examples include, but are not limited to, all B lymphocytes in the B cell developmental pathway starting from the earliest B lymphocyte stem cells through memory B cells, plasma cells, and any immortalized cell lines such as hybridomas.

"Embryonic stem (ES) cells" refer to pluripotent or multi-potent cells that can, when injected into a blastocyst, contribute to many or all tissues of a prenatal, postnatal or adult animal. Animals that result from blastocyst injections are often referred to as "chimeric" animals since their somatic and/or germ cells are often derived from both the blastocyst donors and the injected ES cells.

"Immortalized cells" refer to cells that have been altered in vitro or in vivo to grow and divide indefinitely. Methods of immortalizing cells include, but are not limited to, transforming them with oncogenes, infecting them with oncogenic viruses, culturing them under conditions that select for immortalized cells, subjecting them to carcinogenic or mutating compounds, fusing them with a cell of another immortal cell line, e.g., a myeloma cell, and inactivating tumor suppressor genes.

"Spheroplast" refers to a yeast cell stripped in vitro of its cell wall, resulting in yeast cells with exposed cytoplasmic membranes susceptible to fusion with other cells, e.g., ES cells.

"Germline configuration" refers to the arrangement and spacing of immunoglobulin gene segments before any somatic gene rearrangement has occurred.

"Genetic lesion" refers to any natural or non-natural disruption in genes or loci. Genetic lesions result in the reduction or absence of expression of genes or loci or alternatively result in the expression of gene products so altered so as to eliminate their natural functions. Genetic lesions include, but are not limited to, targeted disruption of gene or locus coding sequences, alterations of cis regulatory elements associated with expression of the genes or loci, alterations of trans regulatory factors associated with expression of the genes or loci, and gross disruptions of whole chromosomes, or regions thereof, comprising the genes or loci.

"cis regulatory elements" generally refer to sequences that regulate the inducible or constitutive expression of gene sequences on the same chromosome under specific conditions or in specific cells. Examples of cellular processes that expression control sequences regulate include, but are not limited to, gene transcription, somatic gene recombination, messenger RNA splicing, protein translation, immunoglobulin isotype switching, protein glycosylation, protein cleavage, protein secretion, intracellular protein localization and extracellular protein homing.

"Substantially complete transgenic immunoglobulin locus" refers to between 50% and 100% of an immunoglobulin locus derived from an animal other than the host animal. In a preferred embodiment, a substantially complete transgenic immunoglobulin locus refers to between 75% and 100% of an immunoglobulin heavy or light chain locus derived from an animal other than the host animal. In a more preferred embodiment, a substantially complete transgenic immunoglobulin locus refers to between 90% and 100% or between 95% and 100% of an immunoglobulin heavy or light chain locus derived from an animal other than the host animal. In a an even more preferred embodiment, a substantially complete transgenic immunoglobulin locus refers to approximately 98 to 100% of an immunoglobulin heavy or light chain locus derived from an animal other than the host animal.

"Substantially inactivated endogenous immunoglobulin loci" refers to an animal having a genetic lesion in its immunoglobulin heavy and light chain loci, resulting in the loss of expression of the loci within the animal. In a preferred embodiment, expression from the inactivated endogenous immunoglobulin loci is between 0% and 30% of wild type expression levels. In a more preferred embodiment, expression from the inactivated endogenous immunoglobulin loci is between 0% and 15% of wild type expression levels. In a most preferred embodiment, expression from the inactivated endogenous immunoglobulin loci is approximately 0% to 5%, more preferably 0% to 1% of wild type expression levels.

A nucleic acid sequence "substantially corresponds", "substantially corresponding" or is "substantially similar" to the nucleic acid sequence of a human Ig heavy chain, $\lambda$ light chain or $\kappa$ light chain locus when (a) the nucleic acid molecule comprising the nucleic acid sequence hybridizes to the nucleic acid molecule comprising a human Ig heavy chain, $\lambda$ light chain or $\kappa$ light chain locus under highly stringent conditions and/or (b) the nucleic acid molecule comprising the nucleic acid sequence exhibits substantial sequence similarity to the nucleic acid molecule comprising a human Ig heavy chain, $\lambda$ light chain or $\kappa$ light chain locus. An example of "high stringency" or "highly stringent" conditions is a method of incubating a polynucleotide with another polynucleotide, wherein one polynucleotide may be affixed to a solid surface such as a membrane, in a hybridization buffer of 6×SSPE or SSC, 50% formamide, 5× Denhardt's reagent, 0.5% SDS, 100 µg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., supra, pp. 9.50-9.55. Substantial sequence similarity indicates that, when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, Methods Enzymol. 183: 63-98 (1990); Pearson, Methods Mol. Biol. 132: 185-219 (2000); Pearson, Methlods Enzymol. 266: 227-258 (1996); Pearson, J. Mol. Biol. 276: 71-84 (1998); herein incorporated by reference).

Yeast artificial chromosomes (YACs) refer to cloning vehicles constructed from elements of yeast chromosomes that allow the vector to be replicated and maintained in yeast cells in vivo. Yeast elements include a centromere, an autonomous replication sequence, a pair of telomeres, yeast selectable markers, and usually a bacterial origin of replication and selectable marker for replication and selection of the YAC vector arms in bacteria. DNA inserts of up to at least 2000 kb can be cloned and maintained using YACs.

"Transgenic animals" refer to animals bearing substantial portions of human immunoglobulin loci. Often, transgenic animals bear homologously targeted endogenous immunoglobulin loci, rendering them incapable of expressing their endogenous immunoglobulin. One example comprises the mice of the XenoMouse® line, e.g., the XenoMouse-L and XenoMouse-KL lines described herein, which are capable of somatic rearrangement of transgenic human immunoglobulin genes, hypermutation of the human variable genes, immunoglobulin gene expression, and immunoglobulin isotype switching. Therefore, the mice of the XenoMouse® line are capable of mounting effective humoral responses to antigenic challenge utilizing the human immunoglobulin gene sequences. Antibodies produced in the mice of the XenoMouse® line are fully human and can be isolated from the animals themselves or progeny thereof, from cultured cells extracted from the animals or progeny thereof, and from hybridomas created from XenoMouse-L and XenoMouse-KL B lymphocytic lines or progeny thereof. Moreover, the rearranged human gene sequences encoding immunoglobulins raised against specific antigenic challenges can be isolated by recombinant means well known in the art.

An "antibody" refers to an intact immunoglobulin or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide.

"Transgenic antibodies" refer to antibodies that are encoded by foreign immunoglobulin loci. For example, in mice of the XenoMouse-L and XenoMouse-KL lines, the human antibody loci encode transgenic antibodies.

"Transgenic monoclonal antibodies" refer to homogenous populations of antibodies that are produced in cloned, immortalized cells, e.g. hybridomas, derived from transgenic animals. For example, hybridomas made from mice of the XenoMouse-L and XenoMouse-KL lines produce transgenic monoclonal antibodies.

The term "isolated protein", "isolated polypeptide", "isolated antibody" or "isolated immunoglobulin" is a protein, polypeptide, antibody or immunoglobulin, respectively, that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide or antibody that is chemically synthesized or synthesized in a cellular system different from the cell from which it naturally originates will be "isolated" from its naturally associated components. A protein or antibody may also be rendered substantially free of naturally associated components by isolation, using protein purification techniques well known in the art. An isolated antibody may be one that is not associated with other naturally-associated antibodies that accompany it in its native state. Examples of isolated antibodies include a human antibody that has been affinity purified using an antigen, Protein A or Protein L, a human antibody that has been synthesized by a hybridoma or other cell line in vitro, and a human antibody derived from a transgenic mouse.

A protein, polypeptide, antibody or immunoglobulin is "substantially pure," "substantially homogeneous" or "substantially purified" when at least about 60 to 75% of a sample exhibits a single species of the protein, polypeptide, antibody or immunoglobulin, respectively. A substantially pure protein, polypeptide, antibody or immunoglobulin will typically comprise about 50%, 60%, 70%, 80% or 90% W/W of a sample, more usually about 95%, and preferably will be over 99% pure. Purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). Thus, an intact IgG antibody has two binding sites. Except in bifunctional or bispecific antibodies, the two binding sites are the same. For secreted IgM antibodies, the basic unit is a pentamer of bivalent antibodies. Thus, each pentameric IgM antibody has ten binding sites. For secreted IgA antibodies, the basic unit is a tetramer of bivalent antibodies. Thus, each tetrameric IgA antibody has four binding sites. The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa ($\kappa$) and lambda ($\lambda$) light chains. Heavy chains are classified as mu ($\mu$), delta ($\delta$), gamma ($\gamma$), alpha ($\alpha$), or epsilon ($\epsilon$), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

B Cell Development

B cell development initiates in the bone marrow with a deletional recombination between a D and J gene. Subsequently, a V gene recombines with the DJ to make a VDJ, which is transcribed, producing a spliced VDJCµ transcript. If the transcript is in-frame, then a µ chain is synthesized upon translation. Similarly, and generally after $V_H DJ_H$ recombination and successful pairing of the µ chain with surrogate light chain, the Ig light chain loci rearrange their V and J gene segments. Successful B cell development in the bone marrow results in B cells expressing IgMκ or IgMλ on the cell surface. In the mouse, 95% of the B cells express IgMκ and 5% express IgMλ; in the human, approximately 60% of the B cells express IgMκ and 40% express IgMλ.

These IgM producing B cells form the primary immune repertoire and perform immune surveillance for recognition of foreign antigens. In the mouse or in humans, these IgM producing B cells can subsequently undergo isotype class-switching from IgM to the IgG or IgA, or IgE isotypes. The frequency of class switching increases during an immune response. Mice and humans each have genes for four different isotypes of IgG. They are IgG1, IgG2a, IgG2b, and IgG3 in the mouse, and IgG1, IgG2, IgG3, IgG4 in the human.

Humans have two IgA isotypes, IgA1 and IgA2, and one IgE isotype. In a mouse, there is, on average, 6500, 4200 and 1200 µg/ml of IgG1, IgG2a, and IgG2b respectively, and 260 µg/ml IgA. In the human, of the total IgG, about 70% is IgG1, 18% is IgG2, 8% is IgG3 and 3% is IgG4. In the total IgA in humans, about 80% is IgA1 and 20% is IgA2.

The Human λ Immunoglobulin Locus

The human λ Ig locus spans 0.9 Mb. There are about 69 Vλ genes segments, of which 36 have open reading frames. Of these, 30 have been detected in transcripts from human peripheral blood lymphocytes (PBL). The Vλ genes fall into 3 clusters that, from 5' to 3', are designated cluster C, cluster B and cluster A. Cluster A contains 14 functional Vλ gene segments and represents about 62% of the expressed repertoire, Cluster B contains 11 Vλ genes, representing 33% of the expressed repertoire, and cluster C contains 5 Vλ genes, representing 5% of the expressed repertoire. The expressed repertoire is based on the frequency of representation of Vλ genes in the repertoire expressed by human PBL. See, e.g., Ignatovich et al., *J. Mol. Biol.,* 268:69-77, 1997, herein incorporated by reference). Ten Vλ gene families are represented in these clusters. The largest family, Vλ III, has 23 members, eight of which are functional. There are seven Jλ-Cλ pairs in the human λ locus, of which four are functional.

Uses of Human Antibodies and Transgenic Animals Producing Them

Administration of mouse or rat antibodies to a human patient is usually ineffective because the presence of mouse- or rat-derived sequences in antibodies may lead to the rapid clearance of the antibodies or to the generation of an immune response against the antibody by a patient. Human antibodies avoid certain of the problems associated with antibodies that possess mouse or rat variable and/or constant regions. Because the creation of human monoclonal antibodies using cells derived from humans was problematic, it was desirable to develop transgenic animals that could produce human antibodies.

Integration of human Ig YAC transgenes into the host chromosomes provides exceptional genetic stability. Integrated human Ig YAC transgenes are stably represented in all the somatic and germline tissue of a transgenic animal, are transmitted from generation to generation with the expected pattern of Mendelian inheritance and are stably maintained in cultured cells, e.g., hybridomas. In contrast, freely segregating human transchromosomes inserted into the nucleus of a host cell, e.g., a mouse ES cell, are known to be genetically unstable and are lost. Chimeric mice can be derived from these ES cells and they can sometimes pass the transchromosome onto offspring. "Transchromosomic" mice derived from these chimeric mice are somatic mosaics, with some cells possessing the transchromosome and others having lost it. The loss is likely to occur because of inefficient capture of the human centromere on the transchromsome by the mouse mitotic and meiotic spindle, with subsequent aberrant segregation of the transchromsomes during mitosis and meiosis. Furthermore, hybridomas from transchromsomic mice are expected to be unstable as well.

Megabase-sized, germline-configuration YAC fragments of the human heavy chain loci and κ light chain loci have been introduced into transgenic mice to produce XenoMouse IIa mice. See Mendez et al. *Nature Genetics* 15:146-156 (1997), Green and Jakobovits *J. Exp. Med.* 188:483-495 (1998), and WO 98/24893, all of which are hereby incorporated by reference in their entirety.

The invention provided herein builds upon the pioneering XenoMouse® technology by providing transgenic animals comprising human λ light chain loci. In one embodiment, the invention provides mice comprising a substantially complete human λ light chain locus or a part thereof. In another embodiment, the transgenic mice further comprise human heavy chain and κ light chain loci. In a preferred embodiment, the transgenic mice further comprise substantially inactivated endogenous heavy chain and κ light chain genes. In yet another preferred embodiment, the transgenic mice further comprise substantially inactivated endogenous heavy chain, κ light chain and λ light chain genes. In humans, approximately 40% of antibodies comprise λ light chains, while the remaining 60% comprise κ light chains. Thus, transgenic mice comprising a human λ light chain locus should be able to produce a human antibody repertoire of a magnitude close to or substantially the same as that found in humans.

YACs Comprising Human λ Light Chain Loci and Host Cells

In one embodiment of the invention, the invention provides a YAC comprising a human λ light chain locus or portion thereof. In general, YACs comprise a yeast centromere, origins of replication, telomeres, and the DNA of interest. Various centromeres or telomeres may be used, particularly the centromeres from yeast chromosomes 4 and 5. In general, the YAC has a selectable marker which allows for selection or screening of cells into which the YAC has been incorporated. In one embodiment, the HPRT gene, more particularly human HPRT, is used as a selectable marker because it permits efficient selection of HPRT-deficient ES cells carrying the YAC. Other known selectable or screenable markers that may be used include the hygromycin resistance gene, the neomycin resistance gene, fl-gal, and GPT.

A YAC comprising all or a part of the human λ light chain locus may be obtained by any method known in the art following the teachings of the specification. In one embodiment, the YAC is isolated by screening an existing YAC library, such as those available from the Centre d'Etude du Polymorphisme Humain (C.E.P.H.), Paris, France; Washington University, St. Louis, Mo.; or other institutional or commercial sources. Alternatively, the YAC may be readily prepared by techniques well known in the art or as described herein. The genomic sequence of the human λ light chain locus is known and portions thereof may be isolated from human genomic DNA using methods such as PCR, restriction digestion and subsequent isolation, mechanical fragmentation and subsequent isolation, or any other method known in the art. An exemplary method for preparing YACs containing a nucleic acid insert of interest may be found in Birren et al., *Genome Analysis: A Laboratory Manual*, Cold Spring Harbor Laboratory Press, 1999. See Vol. 3, Chapter 5, herein incorporated by reference.

A human λ light chain locus or portion thereof may be contained within one or more YAC clones. When the human λ light chain locus is spread across multiple YAC clones, an intact human λ light chain locus may be reconstituted by homologous recombination between YACs with overlapping regions of homology. See the examples infra. In an alternative embodiment, only a portion of the human λ light chain locus may be used.

In a preferred embodiment, the YAC comprises a human λ locus between 500 kb and 0.9 Mb. In a more preferred embodiment, the YAC comprises a human λ locus between 600 kb and 0.9 Mb, even more preferably between 700 kb and 0.9 Mb, and yet more preferably between 800 kb and 0.9 Mb. In an even more preferred embodiment, the YAC comprises a human λ locus that is approximately 0.9 Mb. The YAC may also comprise a λ light chain locus that is substantially similar to the human λ light chain locus.

A number of different types of host cells may be used in the practice of this invention. In one embodiment, the host cell is one that is capable of integrating the YAC DNA into a chromosome. In a preferred embodiment, the host cell is capable of participating in the formation of a transgenic animal. In a more preferred embodiment, the host cell is an ES cell or an oocyte, preferably an ES cell. Such ES cells typically are expanded in culture, remain viable, provide a means for selection after incorporation of foreign DNA, and are competent to repopulate the host, including the germline. The ES cells provided by the invention may be derived from any non-human host, but preferably is a mammalian or avian cell. In one embodiment, rodents, including rats and mice, may provide the ES cells for incorporation of a human λ light chain locus. Other embodiments include ES cells from common laboratory animals, or domestic animals, include rabbits, pigs, hamsters, horses, dogs, sheep, goats, cattle, guinea pigs, and birds such as chickens, turkeys, etc.

The ES cells may have one or more mutations, e.g., they may lack a particular phenotype or have a dominant phenotype. Of particular interest in this invention are ES cells that may be selected using the HPRT gene, the neomycin resistance gene, the hygromycin resistance gene, fl-gal, and/or GPT.

The ES cell may also have substantially inactivated endogenous heavy chain, κ light chain and/or λ light chain loci. In a preferred embodiment, the ES cell comprises both a substantially inactivated endogenous heavy chain locus and a κ light chain locus. In another preferred embodiment, the ES cell comprises a substantially inactivated endogenous λ light chain locus.

Methods of Making Cells and Animals

The invention also provides methods for introducing a human λ light chain locus into non-human host cells and animals. A YAC carrying the human λ light chain locus or portion thereof may be introduced into a host cell, e.g., an ES cell or an oocyte by a variety of methods, including yeast spheroplast:ES cell fusion, microinjection and lipofection. See, e.g., Example 3 and Birren et al., supra, pp. 546-550. In a preferred embodiment, the invention provides a method in which a yeast cell comprising the YAC of interest is fused with an ES cell. After introduction of the YAC into the ES cell, the cells are selected or screened for incorporation of the YAC into the cell's genome using methods known in the art following the teachings of the specification.

Thus, the invention provides a non-human ES cell or progeny thereof, comprising a substantially complete human λ light chain locus or portion thereof. In a preferred embodiment, the ES cell or progeny comprises a substantially complete germline human λ light chain locus.

In another preferred embodiment, the ES cell further comprises a genetic lesion in the J and/or constant regions of one or more of the endogenous immunoglobulin loci of the non-human embryonic stem cell or progeny thereof. In a more preferred embodiment, the genetic lesion is in an immunoglobulin heavy chain J region. In a more preferred embodiment, the lesion is in the J region of both copies of the immunoglobulin heavy chain locus. In another preferred embodiment, the genetic lesion is in an endogenous light chain J region. In a more preferred embodiment, the genetic lesion is in the constant and/or J region of one or both copies of the endogenous κ light chain locus. In another embodiment, the genetic lesion is in the constant and/or J region of one or both copies of the endogenous λ light chain locus. In another embodiment, the genetic lesion comprises a deletion of one or more of the endogenous heavy chain, κ light chain or λ light chain loci. Further, in a preferred embodiment, the genetic lesion comprises replacement of at least a portion of the endogenous heavy chain, κ light chain and/or λ light chain loci with the corresponding substantially complete human heavy chain, κ light chain and/or λ light chain loci by homologous recombination.

In a more preferred embodiment, the non-human ES cell or progeny thereof further comprises genetic lesions in both endogenous copies of an immunoglobulin locus of the non-human ES cell or progeny thereof, wherein the genetic lesions result in the incapacity of both copies of the endogenous immunoglobulin locus to rearrange.

In another preferred embodiment, the genetic lesion is an insertion of a transgenic sequence. In a more preferred embodiment, the genetic lesion results from the targeted disruption of one or more of the endogenous immunoglobulin loci by a selectable marker gene. In another more preferred embodiment, the selectable marker gene is the HPRT gene, the neomycin resistance gene, the hygromycin resistance gene, fl-gal, or GPT. In another more preferred embodiment, the stem cell or progeny thereof is homozygous for the genetic lesion.

Methods for Making Transgenic Animals Comprising a Human λ Light Chain

After selection and screening, the ES cell may be used to create transgenic animals of the invention. See Example 3 infra. In one embodiment, the host animals are a transgenic animal selected from mice, rats, rabbits, pigs, hamsters, horses, dogs, sheep, goats, cattle or guinea pigs. In a preferred embodiment, the host animal is a mouse. In another embodiment, the host animals are transgenic animals containing one or more genetic lesions in the animals' endogenous immunoglobulin loci. In a more preferred embodiment, the host animals are mice of the Xenomouse™ line.

The invention provides a method for producing a transgenic animal, comprising:

a. combining under fusing conditions (a) yeast spheroplasts having incorporated a YAC comprising a substantially complete human λ light chain locus or portion thereof and a selectable marker with (b) ES cells of a host animal;

b. selecting for ES cells that have incorporated the selectable marker and thereby selecting for the human λ light chain locus or portion thereof, whereby the human λ light chain locus or portion thereof and selectable marker are incorporated into the genome of the embryonic stem cells;

c. transferring the selected ES cells into a host blastocyst and implanting the blastocyst in a pseudopregnant animal recipient;

d. allowing the blastocyst to develop to term to produce a chimeric animal carrying the human λ light chain locus or portion thereof; and e. mating the chimeric animal with an animal of the same species to produce the transgenic animal, wherein the transgenic animal has inherited the human λ light chain locus or portion thereof from the chimeric animal.

In a preferred embodiment, the human λ light chain locus is a substantially full-length germline sequence. In another preferred embodiment, the selectable marker is the HPRT gene, the neomycin resistance gene, the hygromycin resistance gene, fl-gal, or GPT. In another preferred embodiment, the ES cell is deficient in endogenous immunoglobulin heavy and λ and/or κ light chain expression. In a more preferred embodiment, the ES cell further comprises a human heavy chain locus and a human κ light chain locus. In another preferred embodiment, the method further comprises mating the heterozygous transgenic animal of step (e) to another transgenic animal heterozygous for the human λ light chain locus to produce a transgenic animal homozygous for the human λ light chain locus.

In yet another preferred embodiment, the transgenic animal heterozygous for the human λ light chain locus is mated to a transgenic animal that has substantially inactivated endogenous immunoglobulin heavy chain and κ light chain loci and, optionally, a substantially inactivated endogenous λ light chain loci, and which transgenic animal comprises human heavy chain and human κ light chain loci. In a preferred embodiment, the human κ light chain and the human λ light chain each comprises V, J and constant region genes and the human heavy chain comprises V, J, D and constant region genes. Transgenic animals heterozygous for the presence of a human λ light chain, human heavy chain and κ light chain loci are selected and mated to each other. Transgenic animals homozygous for the presence of a human λ light chain, heavy chain and κ light chain expression are then selected.

In a preferred embodiment, the transgenic animal progeny are one or more animals of an F1, $F_2$, $F_3$, $F_4$, $F_5$, $F_6$, $F_7$, $F_8$, $F_9$ or $F_{10}$ generation. One particular advantage of the XenoMouse is that it is genetically stable, i.e., the human immunoglobulin genes are maintained in the mice without being deleted for generations. Cell lines or other products made from the mice are also stable. In a preferred embodiment, at least 95% of a population of transgenic animals of the invention are genetically stable for at least three generations, more preferably five generations, even more preferably seven generations or ten generations. In another preferred embodiment, at least 98% or 100% of the population is genetically stable.

In another preferred embodiment, the method described above is used to produce a transgenic animal that is a rat, a dog, a monkey, a goat, a pig, a cow, a hamster, a rabbit, a horse, a sheep, a guinea pig, or a bird. In general, the method involves introducing a YAC into an ES cell from the species of interest, e.g., by spheroplast fusion, introducing the ES cells into a blastocyst and producing a chimeric animal, and then doing appropriate matings to obtain transgenic animals comprising a human A light chain locus. See, e.g., U.S. Pat. No. 5,994,619.

Transgenic Animals Comprising a Human λ Light Chain Locus

Host animals that have incorporated a human λ light chain locus provide the necessary enzymes and other factors involved to produce functional antibodies. Thus, those enzymes and other factors associated with germ line rearrangement, splicing, somatic mutation, and the like will function in the host to make fully transgenic antibodies in the substantial absence of endogenous antibodies.

Therefore, the invention provides chimeric and transgenic animals comprising human λ light chain loci that are capable of expressing human λ light chains. In a preferred embodiment, the invention provides a transgenic non-human animal comprising a human λ light chain locus stably incorporated in the non-human animal, which allows for germline transmission. The animals may be heterozygous or homozygous for the human locus, but preferably are homozygous. These animals may be used for a wide variety of purposes, including production of fully human antibodies and fragments thereof, drug screening, gene therapy, animal models of human diseases and animal models of genetic regulation.

In one embodiment, the invention provides a transgenic animal, comprising a substantially complete human λ light chain locus comprising V, J, and constant region genes. In another embodiment, the invention provides a transgenic animal comprising between 500 kb and 0.9 Mb of the human λ light chain locus. In a more preferred embodiment, the transgenic animal comprises a human λ light chain locus between 600 kb and 0.9 Mb, even more preferably between 700 kb and 0.9 Mb, and yet more preferably between 800 kb and 0.9 Mb. In a more preferred embodiment, the transgenic animal comprises a human λ light chain locus of approximately 0.9 Mb.

In a preferred embodiment, the animal comprising the human λ light chain locus is heterozygous or homozygous for a substantially inactivated endogenous heavy chain locus. In another preferred embodiment, the animal is heterozygous or homozygous for a substantially inactivated endogenous κ light chain locus. In another preferred embodiment, the animal is heterozygous or homozygous for a substantially inactivated endogenous λ light chain locus. In another preferred embodiment, the animal further comprises a human immunoglobulin heavy chain locus comprising V, D, J, and constant region genes. In another preferred embodiment, the animal further comprises a transgenic immunoglobulin-κ light chain locus comprising V, J, and constant region genes.

In a more preferred embodiment, the invention provides transgenic animals, comprising substantially inactivated endogenous immunoglobulin heavy chain and κ light chain loci and, optionally, a substantially inactivated endogenous λ light chain locus; a human immunoglobulin heavy chain locus comprising V, D, J, and constant region genes; a human κ light chain locus comprising V, J, and constant region genes; and a human λ light chain locus comprising V, J, and constant region genes. In a preferred embodiment, the transgenic animal of this embodiment comprises a human λ light chain locus of between 500 kb and about 0.9 Mb of the human λ light chain locus. In a more preferred embodiment, the transgenic animal comprises a human λ light chain locus between 600 kb and 0.9 Mb, even more preferably between 700 kb and 0.9 Mb, and yet more preferably between 800 kb and 0.9 Mb. In an even more preferred embodiment, the human λ light chain locus in the transgenic animal comprises substantially all of the full-length human λ light chain locus.

In another preferred embodiment, the transgenic animal targets the human λ light chain locus for VJ recombination and is capable of expressing the human λ light chain locus. In a preferred embodiment, the human heavy chain locus is capable of being expressed in the transgenic animal. In another preferred embodiment, the human κ light chain locus is capable of being expressed in the transgenic animal.

In another preferred embodiment, the substantial inactivation of the endogenous immunoglobulin heavy chain locus and/or κ light chain locus is a result of introducing a genetic lesion into the locus. In a more preferred embodiment, the substantial inactivation of the endogenous immunoglobulin heavy chain loci comprise a genetic lesion in the J region of the endogenous immunoglobulin heavy chain or light chain loci. In another preferred embodiment, the substantial inactivation of the endogenous light chain loci comprises a genetic lesion in the constant and/or J region of the endogenous light chain loci.

In a preferred embodiment, the transgenic animal is a mouse, a rat, a dog, a monkey, a goat, a pig, a cow, a hamster, a rabbit, a horse, a sheep, a guinea pig, or a bird. In a more preferred embodiment, the transgenic animal is a mouse or rat. In an even more preferred embodiment, the transgenic animal is a mouse.

Although it is preferred that a human λ light chain locus is introduced into a transgenic animal, one having ordinary skill in the art following the teachings of the specification could also introduce a λ light chain locus from a species other than human into a transgenic animal. Examples of desirable species include ape, monkey, other non-human primates, companion animals, such as dogs and cats, and agriculturally-useful animals, such as cattle, horses, sheep, goats and pigs.

Animals that comprise substantially inactivated immunoglobulin heavy chain loci are incapable of generating B lymphocytic immunoglobulin receptors, resulting in an early block in the development of the B lymphocytic lineage. The transgenic immunoglobulin loci complement this deficiency, allowing for the development of B lymphocytic cells or progeny thereof. Therefore, in a preferred embodiment, the transgenic animals described herein that comprise substantially inactivated immunoglobulin loci further comprise a reconstituted primary or secondary B lymphocytic population wherein the level of the population is 5-20% that of a wild type animal, 20-40% that of a wild type animal, 40-60% that of a wild type animal, 60-80% that of a wild type animal, 80-100% that of a wild type animal, or 100-200% that of a wild type animal.

Production of Antibodies and Antibody-Producing Cells

Transgenic animals of the invention, or B lymphocytes derived therefrom, may be used to produce isolated monoclonal and/or polyclonal antibodies comprising a human λ light chain. Further, B lymphocytes derived from animals of the invention may be used to create cell lines that produce monoclonal antibodies. In one embodiment, the B lymphocytes are immortalized. Immortalization can be accomplished by any means known in the art, including but not limited to: fusion to myeloma cells to produce hybridomas; transfection with oncogenes; infection with oncogenic viruses; and inactivation of tumor suppressor genes. Immortalized cells may be grown in continuous culture for production of antibodies or may be introduced into the peritoneum of a compatible host for production of ascites containing antibodies of interest.

Alternatively, rearranged genes encoding the heavy chain and light chain of an antibody of interest can be isolated from primary cells derived from an immunized transgenic animal of the invention or from immortalized derived from such primary cells and expressed recombinantly. Rearranged antibody genes can be reverse transcribed from appropriate mRNAs to produce cDNA. Nucleic acid molecules encoding heavy and light chains can be inserted into expression systems contained on vectors and transfected into standard recombinant host cells. As described below, a variety of such host cells may be used, the main criteria being compatibility with the expression control sequences.

The production of the antibody is then undertaken by culturing the modified recombinant host under conditions appropriate for the growth of the host cells and the expression of the coding sequences. The antibodies are then recovered from the culture. Preferably, the expression system is designed to include signal peptides so that the expressed antibodies are secreted into the culture medium. Intracellular production, however, is also possible.

In one preferred embodiment, an transgenic animal of the invention is immunized with an antigen of interest, primary cells, e.g., spleen or peripheral blood cells, are isolated from an immunized transgenic animal and individual cells producing antibodies specific for the desired antigen are identified. Polyadenylated mRNA from each individual cell is isolated and reverse transcription polymerase chain reaction (RT-PCR) is performed using sense primers that anneal to variable region sequences, e.g., degenerate primers that recognize most or all of the FRI regions of human $V_H$, and Vλ genes, and antisense primers that anneal to constant or joining region sequences. The $V_H$, and Vλ cDNAs are then cloned and expressed in any suitable host cell, e.g., a myeloma cell, as chimeric antibodies with respective immunoglobulin constant regions, such as the heavy chain and λ constant domains. See Babcook, J. et al., Proc. Natl. Acad. Sci. USA 93: 7843-48, 1996, herein incorporated by reference.

In another embodiment, advantage can be taken of phage display techniques to provide libraries containing a repertoire of antibodies with varying affinities for a desired antigen. For production of such repertoires, it is unnecessary to immortalize the B cells from the immunized animal. Rather, the primary B cells can be used directly as a source of DNA. The mixture of cDNAs obtained from B cell, e.g., derived from spleens, is used to prepare an expression library, for example, a phage display library transfected into E. coli. The resulting cells are tested for immunoreactivity to the desired antigen. Techniques for the identification of high affinity human antibodies from such libraries are described by Griffiths et al, EMBO J., 13:3245-3260 (1994); Nissim et al., ibid, pp. 692-698 and by Griffiths et al., ibid, 12:725-734. Ultimately, clones from the library are identified which produce binding affinities of a desired magnitude for the antigen and the DNA encoding the product responsible for such binding is recovered an manipulated for standard recombinant expression. Phage display libraries may also be constructed using previously manipulated nucleotide sequences and screened in a similar fashion. In general, the cDNAs encoding heavy and light chains are independently supplied or are linked to form Fv analogs for production in the phage library.

The phage library is then screened for the antibodies with highest affinity for the antigen and the genetic material recovered from the appropriate clone. Further rounds of screening can increase affinity of the original antibody isolated.

In one embodiment, the invention provides a method for producing polyclonal human antisera and isolated polyclonal antibodies comprising a human λ light chain. The method comprises the steps of immunizing a transgenic animal of the invention with an antigen of interest, allowing the transgenic animal to mount an immune response to the antigen, isolating the serum from the animal to obtain a polyclonal human antisera, and, optionally, isolating the polyclonal antibodies from the antisera. One may obtain isolated antisera and isolated polyclonal antibodies using techniques well-known in the art. See, e.g., Harlow et al., supra. In one embodiment, the antibodies are isolated using, e.g., an affinity column having an Fc binding moiety such as protein A or protein G. One may further produce antibody fragments, such as Fab, Fab' and $F(ab')_2$ fragments using methods known in the art. See, e.g., Harlow et al., supra.

The invention provides methods for producing a cell line that produces a human monoclonal antibody or a fragment thereof directed to a specific antigen, comprising:

a. immunizing the transgenic animals described herein with an antigen of interest;

b. allowing the transgenic animal to mount an immune response to the antigen;

c. isolating B lymphocytes from the transgenic animal;

d. immortalizing the B lymphocytes;

e. creating individual monoclonal populations of the immortalized B lymphocytes; and f. screening the immortalized B lymphocytes to identify an antibody directed to the antigen.

In a preferred embodiment, the immortalizing step is achieved by fusing the B lymphocyte with an appropriate myeloma cell line, such as NSO-bcl2 line [S. Ray, et al., Proc. Natl. Acad. Sci. USA, 91:5548-5551 (1994)] or P3-X63-Ag8.653 cells, available from the ATCC, to produce a hybridoma cell line. In another preferred embodiment, the immortalized B lymphocytes are screened by assaying the supernatant produced by the cells for the presence of the desired antibody. The assaying step typically is an ELISA or an radioimmunoassay (RIA), although any screening method may be used. In a preferred embodiment, the invention provides an isolated monoclonal antibody produced by the methods described herein.

In another aspect, the invention provides a primary cell or progeny thereof derived from the transgenic animals described herein. The invention also provides an immortalized cell or progeny thereof derived from the transgenic animals described herein. In a preferred embodiment, the immortalized cell or progeny thereof is of B lymphocyte origin. In a more preferred embodiment, the immortalized cell is a hybridoma. In another preferred embodiment, the immortalized cell is derived from a mouse cell, a rat cell, a dog cell, a monkey cell, a goat cell, a pig cell, a cow cell, a hamster cell, a rabbit cell, a horse cell, a sheep cell, a guinea pig cell, or a bird cell.

The invention provides an antibody repertoire produced by the transgenic animals described above that comprise between $7 \times 10^5$ to $1 \times 10^{11}$ different antibody species. In another more preferred embodiment, the antibody repertoire comprises between $1 \times 10^5$ to $1 \times 10^7$ different antibody species. In another more preferred embodiment, the antibody repertoire comprises between $1 \times 10^7$ to $1 \times 10^9$ different antibody species. In another more preferred embodiment, the antibody repertoire comprises between $1 \times 10^9$ to $1 \times 10^{11}$ different antibody species.

The invention provides an antibody derived from the transgenic animals described herein, wherein the antibody has a dissociation constant of less than $1 \times 10^{-7}$ M. In a preferred embodiment, the dissociation constant is less than $1 \times 10^{-8}$ M, more preferably less than $1 \times 10^{-9}$ M, more preferably less than $1 \times 10^{-10}$ M, more preferably less than $1 \times 10^{-11}$ M, and even more preferably less than $1 \times 10^{-12}$ M or $1 \times 10^{-13}$. In general, the antibody will have a dissociation constant between $1 \times 10^{-7}$ to $1 \times 10^{-12}$ M.

It is predicted that the specificity of antibodies (i.e., the ability to generate antibodies to a wide spectrum of antigens and indeed to a wide spectrum of independent epitopes thereon) is dependent upon the variable region genes in the human heavy chain ($V_H$), κ light chain (Vκ) and λ light chain (Vλ) loci. The human heavy chain genome includes approximately 95 $V_H$ genes of which 41 are functional genes encoding variable regions of the human heavy chain of immunoglobulin molecules. The human κ light chain locus includes approximately 40 Vκ genes of which 25 are functional and the human λ light chain locus comprises approximately 69 Vλ genes of which 30 are functional and have been found used in rearranged human Igλ transcripts. The human heavy chain and light chain loci further comprise a number of different functional J regions and, for the human heavy chain, a number of different functional D regions. See Table 1.

Provided in accordance with the present invention are transgenic mice comprising all or a portion of the human λ light chain locus, wherein a portion is greater than 60%, more preferably greater than 70% or 80%, and even more preferably greater than 90% or 95%. Preferably, the human λ locus includes at least two and more preferably all three λ gene clusters. In a preferred embodiment, the λ locus includes genes from Vλ gene families I, IV-VII, IX and X. In a more preferred embodiment, the λ locus includes genes from all ten Vλ gene families.

The invention further comprises a transgenic mice having a substantial portion of a human heavy chain locus. Still further, the transgenic animal comprises a human κ light chain locus. In preferred embodiments, therefore, greater than 10% of the human $V_H$ and $V_κ$ genes are present. More preferably, greater than about 20%, 30%, 40%, 50%, 60%, or even 70% or greater of $V_H$ and $V_κ$ genes are present. In a preferred embodiment, constructs including 32 genes from the proximal region of the Vκ light chain locus, 66 genes on the $V_H$ heavy chain locus and 69 genes of the Vλ light chain locus are used. As will be appreciated, genes may be included either sequentially, i.e., in the order found in the human genome, or out of sequence, i.e., in an order other than that found in the human genome, or a combination thereof. Thus, by way of example, an entirely sequential portion of either the $V_H$, Vκ and Vλ loci may be used, or various V genes in the $V_H$, Vκ and Vλ loci may be skipped while maintaining an overall sequential arrangement, or V genes within $V_H$, Vκ and Vλ loci can be reordered. In a preferred embodiment, the entire inserted locus is provided in substantially germline configuration as found in humans. The inclusion of a diverse array of genes from the $V_H$, Vκ and Vλ loci leads to enhanced antibody specificity and ultimately to enhanced antibody affinities.

Further, preferably such mice include the entire $D_H$ region, the entire $J_H$ region, the human mu constant region, and can additionally be equipped with other human constant regions for the coding and generation of additional isotypes of antibodies. Such isotypes can include genes encoding $γ_1$, $γ_2$, $γ_3$, $γ_4$, α, ε, and δ and other constant region encoding genes with appropriate switch and regulatory sequences. As will be appreciated, and as discussed in more detail below, a variety of switch and regulatory sequences can be appropriately utilized in connection with any particular constant region selection.

Table 1 indicates the diversity of antibody combinations that are possible in humans, based strictly on random V-D-J joining and combination with κ light chains, without consideration of N-addition, deletions or somatic mutation events. Based on these considerations, there are greater than $1 \times 10^{-6}$ possible antibody combinations in humans, of any particular isotype.

TABLE 1

| Region | Heavy Chain | κ Light Chain | λ Light Chain |
|---|---|---|---|
| Functional Variable "V" | ~41 | 25 | 30 |
| Functional Diversity "D" | ≧23 | — | — |
| Joining "J" | 6 | 5 | 4 |
| Combinations (V × D × J) | 5,658 | 125 | 120 |
| Total Combinations (HC Combinations × LC Combinations) | | $1.39 \times 10^6$ | |

TABLE 2

| (V genes in XM-KL) | | | |
|---|---|---|---|
| Region | Heavy Chain | κ Light Chain | λ Light Chain |
| Functional Variable "V" | 34 | 18 | 30 |
| Functional Diversity "D" | 23 | — | — |
| Joining "J" | 6 | 5 | 4 |
| Combinations (V × D × J) | 4,692 | 90 | 120 |
| Total Combinations (HC Combinations × LC Combinations) | | $.99 \times 10^6$ | |

The calculation provided in Table 1 does not take into account N-addition or somatic mutation events. Therefore, it will be appreciated that mice in accordance with the invention offer substantial antibody diversity.

Increasing the variety and number of variable regions by including the variable regions of the human λ light chain locus, increases both antibody diversity and antibody specificity. Transgenic animals according to this invention thus are able to mount an immune response to a wide array of antigens including a wide array of epitopes upon individual antigens or immunogens. Antibodies produced in accordance with the present invention also possess enhanced affinities.

Nucleic Acids, Vectors Host Cells and Recombinant Methods of Making Antibodies

The invention provides a nucleic acid molecule isolated from a transgenic animal, wherein the isolated nucleic acid molecules encode a human λ light chain polypeptide or an antigen-binding portion thereof. In a preferred embodiment, the nucleic acid molecule is isolated from a B lymphocyte or progeny thereof that produces the human λ light chain. In a preferred embodiment, the progeny of the B lymphocyte is a hybridoma. In another preferred embodiment, the isolated nucleic acid molecules comprise the sequence encoding between one to three of the CDR regions of the human antibody. In a preferred embodiment, the isolated nucleic acid encodes a human λ light chain polypeptide or an antigen-binding portion thereof that binds to a specific antigen of interest.

In another preferred embodiment, the invention provides vectors comprising the nucleic acid molecules described herein or a fragment thereof. In a more preferred embodiment, the vector further comprises expression control sequences operably linked to the nucleic acid molecule. The invention also provides a host cell comprising a nucleic acid molecule isolated from a transgenic animal that encodes a human λ light chain or an antigen-binding portion thereof that specifically binds to an antigen of interest; or a vector comprising the nucleic acid molecule.

The invention further provides isolated host cells comprising a nucleic acid molecule that was isolated from a transgenic animal and encodes a human heavy chain or the antigen-binding portion thereof and an isolated nucleic acid molecule that encodes a human λ light chain or an antigen-binding portion thereof that specifically binds to an antigen of interest, or a vector or vectors comprising the nucleic acid molecules.

In a preferred embodiment, the host cells are hybridoma cells, bacterial cells, yeast cells, insect cells, amphibian cells and mammalian cells. In a more preferred embodiment, the host cells are mouse cells, rat cells, dog cells, monkey cells, goat cells, pig cells, cow cells, hamster cells, rabbit cells, horse cells, sheep cells, guinea pig cells, or bird cells. In a more preferred embodiment, the mammalian cells are HeLa cells, NIH 3T3 cells, CHO cells, 293 cells, BHK cells, VERO cells, CV-1 cells, NS/0 cells, or COS cells.

The invention provides methods of recombinantly producing a human λ light chain or an antigen-binding portion thereof, or both the human λ light chain and a human heavy chain or an antigen-binding portion thereof, that was identified from a transgenic animal and specifically binds to an antigen of interest, comprising the step of cultivating the host cells described herein under conditions in which the nucleic acid molecules are expressed.

The invention provides non-human transgenic animals comprising the nucleic acid molecules described herein, wherein the non-human transgenic animal expresses the nucleic acid molecule.

The invention provides non-human transgenic animals comprising an isolated nucleic acid molecule that encodes an immunoglobulin heavy chain or an antigen-binding portion thereof and an isolated nucleic acid molecule that encodes an λ light chain or an antigen-binding portion thereof of a human antibody that specifically binds to an antigen of interest, wherein the animal expresses the nucleic acid molecules. In a preferred embodiment, the non-human transgenic animals described herein are mice, rats, dogs, monkeys, goats, pigs, cows, hamsters, rabbits, horses, sheep, guinea pigs, or birds. In another preferred embodiment, the human antibody resulting from expression of the isolated nucleic acid molecules or a portion thereof is expressed on the surface of cells derived from the animal's B lymphocytes or progeny thereof. In another preferred embodiment, the human antibody resulting from expression of the isolated nucleic acid molecules or a portion thereof is secreted into the lymph, blood, milk, saliva, or ascites of the animal.

The following examples are offered by way of illustration and not by way of limitation. The media and general methods used herein are described in Birren et al., *Genome Analysis: A Laboratory Manual*, Cold Spring Harbor Laboratory Press, 1999, herein incorporated by reference. The media and general methods for YAC cloning, isolation, manipulation and analysis are described in Birren et al., supra, Volume 3, Chapter 5 and Appendices 1-5, herein incorporated by reference.

EXAMPLE 1

Identification of YACs Comprising Human Immunoglobulin-λ Light Chain Sequences

YACs comprising parts of the human immunoglobulin-λ light chain locus and probes for all $V_\lambda$ and $C_\lambda$ were obtained from the Medical Research Center (MRC, Edinburgh, UK). The L1 YAC and L2 YAC were initially analyzed to (1) confirm the presence of the correct human immunoglobulin-λ loci; (2) assess the stability of the immunoglobulin-λ gene sequences; (3) determine the orientation of the immunoglobulin-λ gene sequences; and (4) confirm the presence of the yeast markers in the YACs.

Yeast containing the YACs were streaked for single colonies on SC-URA agar plates (see Birren et al., supra, Vol. 3, pp. 586-87) and incubated for three to four days at 30° C. until colonies appeared. Single colonies were inoculated into 5 mL of SC-URA liquid media and grown to saturation. Freezer stocks and DNA preparations were made (yeast plugs). See Birren et al., supra, Vol. 3, pp. 391-395.

To confirm the presence and integrity of the human immunoglobulin-λ light chain DNA, undigested L1 and L2 YAC DNA was subjected to pulse field gel electrophoresis (PFGE) using a CHEF-DRII apparatus (Bio-Rad, Hercules, Calif.). The DNA was electrophoresed through 0.8% agarose/0.5× TBE gels at 200 volts and compared to a multimerized λ DNA ladder used as a size marker (New England Biolabs Cat. No. 340). The gels were exposed to alternating 60 second pulses for 15 hours, followed by 90 second pulses for 10 hours. After electrophoresis, the gels were stained with EtBr, photographed, depurinated in 0.2 N HCl and denatured with NaOH.

The YAC DNA embedded in the gels was transferred to a nylon membrane (Genescreen, NEN, Boston, Mass.) and the membrane probed using standard techniques (see, e.g., Maniatis et al., Molecular Cloning: A Laboratory Manual, Cold Spring Harbor Press, 1989) to determine the size of the L1 and L2 YACs. The probe was a $^{32}$P-labeled TRP gene, a 5.4 kb EcoRI/BamHI fragment of pYAC4 (GenBank Accession No. U01086) from nucleotides 6008 to 11454. The Southern blot analysis revealed that the L1 YAC was approximately 1 Mb and the L2 YAC was approximately 450 kb. Moreover, the immunoglobulin-λ light chain sequence in the L1 YAC was found to be stable (see Birren et al., supra, Vol. 3, pp. 586-87) for 48 hours.

Following analysis of the YAC large-scale structure, the L1 and L2 YAC DNA molecules were analyzed by EcoRI digestion and Southern blotting to confirm the presence of the germline Vλ genes. When the L1 YAC DNA was probed with $V_\lambda$ sequences obtained from the Medical Research Council, bands consistent with those predicted by the disclosure of Frippiat et al. *Hum. Mol. Genet.* 4:987-991 (1995), were observed, confirming that the L1 YAC had most of the $V_\lambda$ genes. Probes may also be readily generated by someone having ordinary skill in the art. See, e.g., Frippiat et al., pg. 984, supra, Kawasaki et al., *Genome Res.* 7:250-261 (1997); Williams et al., *J. Mol Biol.* 264:220-232 (1996), pp. 226-229, which describes probes derived from $V_\lambda$ genes. However, the L1 YAC contained a rearrangement on the 3' end at the $V_\lambda$/JC junction, as revealed by the loss of an AscI site, and deletion of $V_\lambda$ genes, 3a2, 2a1 4c, 3q and 3r by the convention of Williams et al., *J. Mol. Biol.* 264:220-232 (1996). See FIG. 1.

When the L2 YAC was probed with $V_\lambda$ sequences, 11 $V_\lambda$ genes from the 3' end of the human immunoglobulin-λ light chain locus were detected, including the germline $V_\lambda$ region that was rearranged on the 3' end of the L1 YAC. The L2 YAC was also found to contain germline $J_\lambda$ and $C_\lambda$ genes.

The L1 and L2 YAC arm orientations were determined by Southern blot analysis. The L1 and L2 YAC DNAs were digested with PmeI, NotI, AscI, RsrII, and MluI, the digested DNA separated by PFGE and then transferred to a nylon membrane, essentially as described above. The blots were probed sequentially with a $C_\lambda$ sequence, the immunoglobulin-λ light chain enhancer, an ampicillin gene sequence, and an URA3 gene sequence and compared to a reference orientation. See Kawasaki et al., *Genome Res.* 7:250-261 (1997). See also Birren et al., supra, Vol.3, pp. 417-420. The orientations of the L1 and L2 YAC arms were opposite to each other and thus inappropriate for direct recombination.

EXAMPLE 2

Construction of a YAC Comprising a Full-Length Human Germline Immunoglobulin-λ Locus To reconstruct the entire germline human immunoglobulin-λ light chain locus on a single YAC, the L2 YAC sequences had to be recombined with the L1 YAC sequences in the proper orientation. For numbering of nucleotides in the λ locus, the complete nucleotide sequence of Kawasaki, supra, was used. The contigs of Kawasaki were accessed from Genbank (www.ncbi.nlm.nih.gov/Genbank/GenbankSearch.html) and re-assembled into a contiguous nucleic acid sequence of 1 Mb using the Vector NTI software (InforMax, North Bethesda, Md.). This sequence covers approximately 125 kb 5' of the first $V_\lambda$ gene and includes through the 3' enhancer.

Construction of pYAC-5' and pYAC-3'

Figure 2:
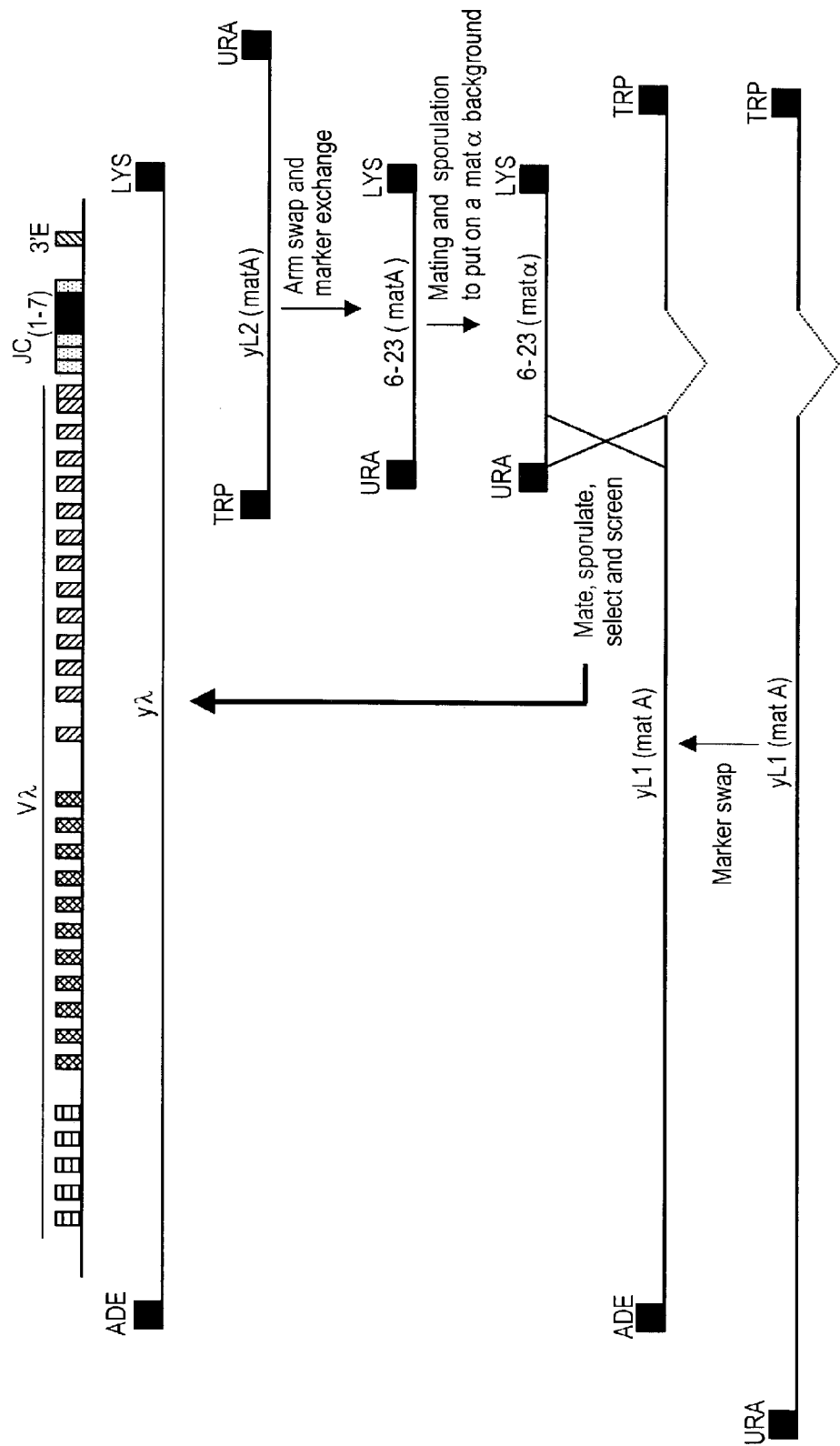
FIG. 2 shows the reconstruction of the human immunoglobulin λ locus into the YAC designated yL.
Figure 6A:
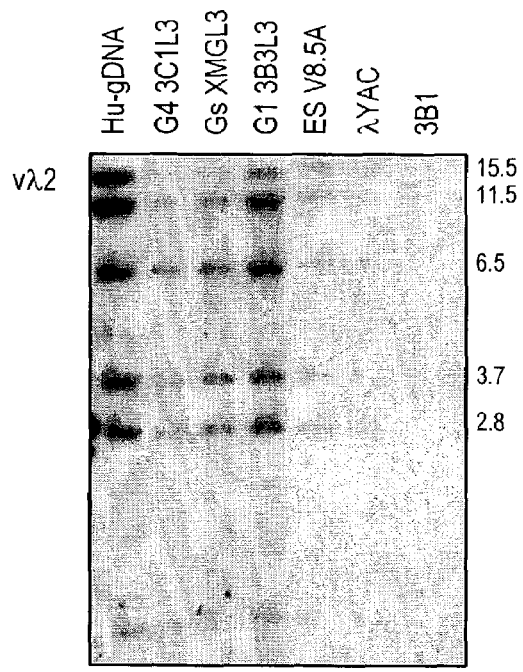
FIGS. 6A-G are Southern blot analyses demonstrating human germline immunoglobulin λ gene integration in embryonic stem (ES) cells and XenoMouse strains.
Figure 6B:
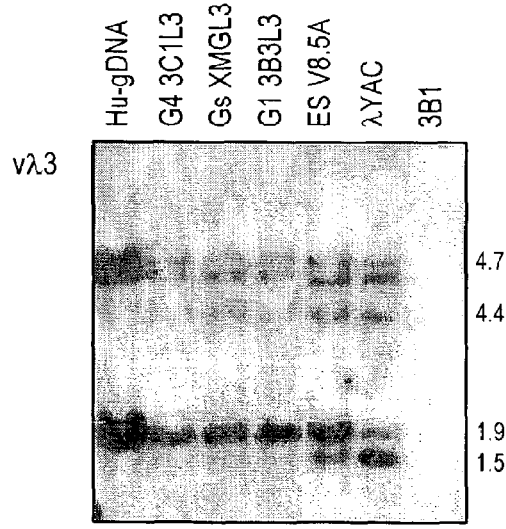
Figure 6C:
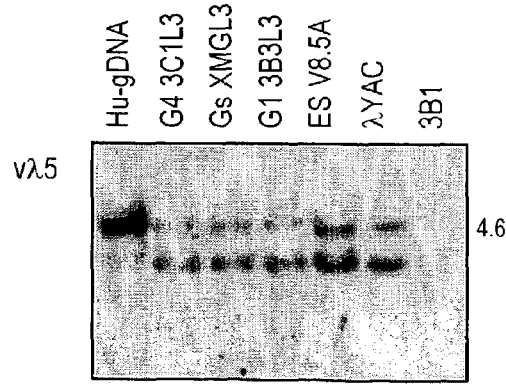
Figure 6D:
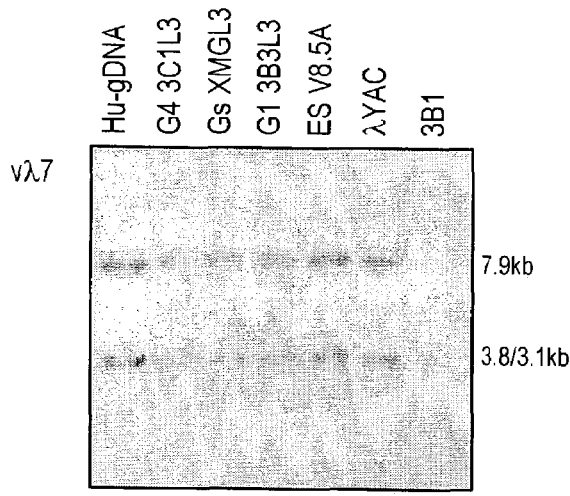
Figure 6F:
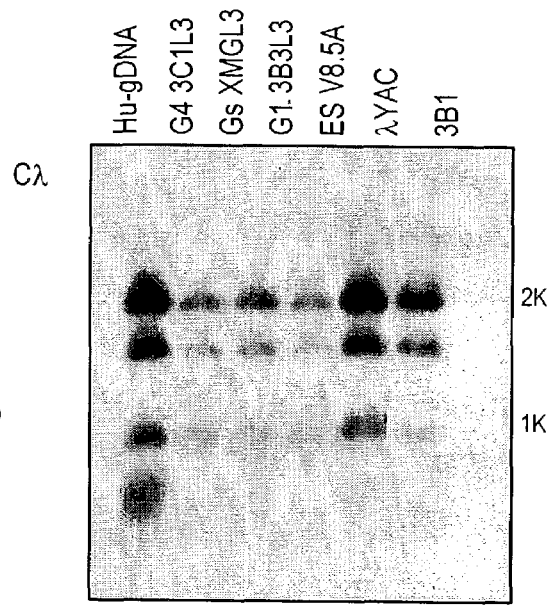
Figure 6E:
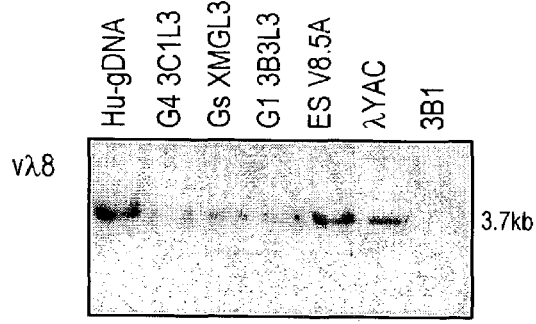
Figure 6G:
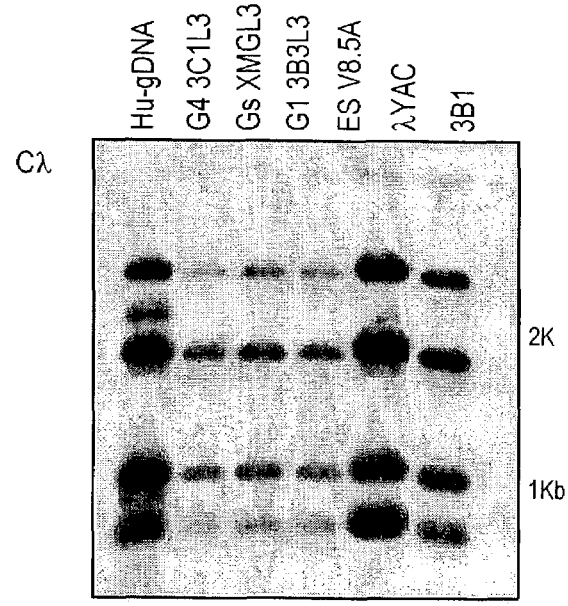

The first step was to alter the L2 YAC to comprise shortened arms that were appropriate for recombination with the L1 YAC. See FIG. 2. We constructed targeting vectors for both the 5' and the 3' ends of the L2 YAC (pYAC-5' and pYAC-3', respectively) in order to build a YAC of 115 kb.

To construct pYAC-5' for targeting the 5' end of the L2 YAC, a 1,330 bp fragment portion of the L2 YAC DNA was amplified by PCR and then cloned into the pCR2.1 cloning vector (Invitrogen, Carlsbad, Calif.). For PCR, the 5' primer sequence used was 5'-CGG ACC GCC TCA TTT GTT GTC AGA TCA TG-3' (SEQ ID NO: 1) and contained a synthetic RsrII site for directional cloning. The 3' primer sequence used was 5'-GGC CGG CCA GCA GAA TAC ATG TTA TCT T-3' (SEQ ID NO: 2) and contained a synthetic FseI site for directional cloning.

The targeting vectors were constructed in pYAC4, a vector commonly used to construct YACs, see Kuhn and Ludwig, *Gene* 141:125-7 (1994), which contains ARS, CEN, telomere, URA and TRP sequences. To construct pYAC-5', pYAC4 was digested with NotI and ligated to annealed linkers, which had the restriction sites NotI (inactivated)-RsrII-NruI-ClaI-FseI-NotI and the sequence 5'-GGC CAT CGG ACC GTC GCG AAT CGA TGG CCG GCC GC-3' (SEQ ID NO: 3), and 5'-GGC CGC GGC CGG CCA TCG ATT CGC GAC GGT CCG AT-3' (SEQ ID NO: 4). This produced a pYAC4-derived vector having a multiple cloning site comprising RsrII, NruI, ClaI, FseI and NotI sites. The orientation of the linkers was confirmed by a NotI/SpeI digest. The L2 YAC 5' homology fragment was then isolated as a RsrII/FseI cassette from pCR2.1 and ligated into the RsrII and FseI sites of the pYAC4-derived vector. The orientation and insert of pYAC-5' was confirmed by restriction digest analysis.

To construct pYAC-3', a 1,310 bp fragment of the L2 YAC 3' of the 3' enhancer was amplified by PCR and cloned into the pCR2.1 cloning vector. For PCR, the 5' primer sequence was 5'-ACG CGT TGA TGA GCA ACC ACA GGC CT-3' (SEQ ID NO: 5) and contained a synthetic MluI site for directional cloning. The 3' primer sequence was 5'-GGC CGG CCA GTC CAT CCT GGC TTC CTT C-3' (SEQ ID NO: 6) and contained a synthetic FseI site for directional cloning. pYAC4 was digested with NotI and BamHI and the 5.5 kb vector fragment containing the CEN, ARS, and TRP and telomere regions was isolated by agarose gel electrophoresis and ligated with annealed linkers having the restriction sites NotI (inactivated)-BglII-FseI-NruI-ClaI-MluI-NotI-BamHI (inactivated) and the sequences 5'GGC CAT AGA TCT GGC CGG CCT CGC GAA TCG ATA CGC GTG C-3' (SEQ ID NO: 7), and 5'-GAT CGC GGC CGC ACG CGT ATC GAT TCG CGA GGC CGG CCA GAT CTA T-3' (SEQ ID NO: 8). The L2 YAC 3' homology fragment was then isolated as a NotI/BamHI cassette and ligated into the NotI and BamHI sites of the resultant vector. The resulting intermediate plasmid was termed pYAC-3'int 2 and was confirmed by restriction digest analysis. Because the linker was directionally cloned, the linker orientation was not confirmed.

Unlike pYAC4, pYAC-3'int 2 lacks the URA arm and is approximately 5 kb smaller. pYAC-3' int2 was digested with AatII and an AatII-EcoRI-AatII linker was cloned into the AatII site. To construct the final pYAC-3' targeting vector, the resulting plasmid was digested with EcoRI and XbaI, which removes part of the TRP gene, and ligated with a 4.5 kb EcoRI/XbaI cassette containing the LYS2 gene from the pLUS plasmid (ATCC No. 77407; Hermanson et al., *Nucleic Acids. Res.* 19:4943-4948 (1991)).

Construction of Clone 6-23

The yeast comprising the L2 YAC were transformed with the pYAC-5' and pYAC-3' targeting vectors. The yeast were first incubated in SC-URA liquid medium for 24 hours at 30 deg C., then incubated in YPDA medium at 30° C. for 4-5 hours. The cells were transformed simultaneously with BamHI-linearized pYAC-3' and the 5 kb BamHI/FseI fragment (URA arm) from pYAC-5' using the LiAc transformation procedure. See Scheistl et al., *Curr. Genet.* 16: 339-346 (1989). The transformants were plated on SC-LYS agar plates, which are incubated at room temperature for 4-5 days until clones appeared.

Clones were picked and grown on SC-LYS and SC-TRP plates to identify recombinant YACs, which are URA+, LYS+, TRP−. See FIG. 2. Following clone recovery, the YAC DNA was isolated and tested by PFGE to estimate the size of modified L2 YAC and by Southern blot analysis using the $V_\lambda$ probes to confirm the presence of $C\lambda$ genes (Hind III and BamHI digests), $V_\lambda$ genes (EcoRI digests), and the $\lambda$ enhancer (StuI digests). The shortened L2 YAC is approximately 115 kb in size and is designated as clone 6-23. See FIG. 2.

Genetic Analysis of Clone 6-23

The YAC 6-23 was transferred into the YPH925 strain (MATa ura3-52 lys2-801 ade2-101 his3, ATCC #90834). YPH925 and 6-23 YAC (MATa) were grown overnight on YPDA plates at 30° C. in patches of approximately 1 cm². The next morning they were mated on a YPDA plate and grown at 30° C. for 6 hours. The resulting mixture of haploids and diploids was transferred to SC-URA-LYS-HIS plates that provide selection against both haploids, but not the resultant diploids, due to the complementarity of the two HIS alleles in the haploid strains. The cells were incubated for 2 days at 30° C. until single colonies appeared. Six independent colonies were picked, grown in 1 cm² patches on YPDA plates, incubated overnight, replica plated onto sporulation plates and incubated at room temperature for 4-5 days. See, Birren et al., supra, Vol. 3, pp. 495-501.

Cells were examined microscopically for sporulation, which was over 5%. Sporulated cells were grown for 4-5 days on SC-URA-LYS plates supplemented with canavanine and cycloheximide to prevent diploid formation and to select for cells bearing the 6-23 YAC. Colonies were picked and grown in SC-LYS media for further analysis.

The mating type was checked by a PCR assay designed to identify mata clones. See Birren et al., supra, Vol. 3, pp. 442. The primer sequences were 5'-AGT CAC ATC AAG ATC GTT ATG G-3' (SEQ ID NO: 9); 5'-GCA CGG AAT ATG GGA CTA CTT CG-3' (SEQ ID NO: 10); and 5'-ACT CCA CTT CAA GTA AGA GTT TG-3' (SEQ ID NO: 11). See, Huxley et al., *Hum. Mol. Genet.* 5: 563-569 (1990). Approximately half of the clones were the a-mating type and half were the a-mating type.

To confirm that the MATa clones retained an intact 6-23 YAC, they were further analyzed by PFGE and Southern blot analysis as described above in Example 1. The results showed that the 6-23 YAC remained intact and the strains were ready for mating with a L1 YAC clone.

The 6-23 clone was further analyzed for resistance to canavinine (CAN) and cycloheximide (CYH), used for selection of haploids following mating with a L1 YAC-bearing clone and sporulation. See Birren et al., supra, Vol. 3, pp. 495-501.

Introduction of bcl-a into pYA C-5'

In order to determine the number of copies of the immunoglobulin-λYAC following introduction into ES cells and into the germline of transgenic mice, a truncated bcl-a gene was also cloned into pYAC-5'. The gene was obtained by PCR amplification of mouse DNA using a first primer of sequence 5'-GGG GTA TTT GTG GAA TTA CTT-3' (SEQ ID NO: 12) and a second primer of sequence 5'-CCC ATC TGG ATT TCT AAG TGA-3' (SEQ ID NO: 13). The PCR-amplified product was then cloned into the pCR2.1 cloning vector. The plasmid containing the bcl-a gene was then digested with NsiI, the NsiI-NsiI fragment was discarded, and the plasmid religated to create a 173 bp bcl-a sequence. The orientation of the truncated bcl-a gene in the pCR2.1 was determined by restriction digest analysis.

The resulting plasmid was digested with BamHI, the ends filled with Klenow fragment and digested with ApaI. The 170 bp bcl-a fragment was isolated and cloned into the NruI and ApaI sites of the pYAC-5' vector as described in Example 2 above.

Introduction of HPRT into the L1 YAC

Non-human animal ES cell fusions with yeast spheroplasts bearing YACs to create ES cells bearing human immunoglobulin-λ light chain loci is facilitated by YACs that contain a mammalian selectable marker, e.g., HPRT, for selection in the ES cells negative for endogenous HPRT function. Therefore, to make a YAC that will support efficient detection of the introduction of a human immunoglobulin-λ light chain locus into a mouse ES cell, a targeting vector for introducing HPRT into the L1 YAC was constructed. The strategy chosen also results in the shortening of L1 YAC by targeting a region approximately 22 kb directly upstream of the most 5' $V_\lambda$ gene, $V_\lambda$ 1-27. The pREP plasmid (Mendez et al., *Genomics* 26:294-307 (1995)) containing the ADE and HPRT selectable markers was partially digested with BamHI, the overhangs filled with Klenow fragment to create blunt ends and religated. The BamHI site that was eliminated was determined by a digestion with BamHI and NotI. The ADE2 and HPRT genes were cloned as a BamHI/NotI cassette into the pYAC-5' BamHI/NruI sites.

Next, a PCR-product of 950 bp from the region 5' of $V_\lambda$ 1-27 was amplified from the L1 YAC. This sequence was amplified by PCR using a 5' primer having the sequence 5'-CGG ACC GCA GAG TGA GCC AAG ATT GTA-3' (SEQ ID NO: 14) and having an RsrII site, and a 3' primer of sequence 5'-GGC CGG CCT GTG CTG CTG GAT GCT GTT-3' (SEQ ID NO: 15) and having an FseI site. This fragment was cloned into the RsrII and FseI sites of the pYAC-5' plasmid. The vector was then linearized with NotI and transformed into yeast containing the L1 YAC by LiAc transformation. The transformed yeast cells were plated on SC-ADE plates to select for the targeted YAC. Colonies were picked and the YAC in yeast clones were analyzed by PFGE and Southern blot analysis as described above in Example 1. The $V_\lambda$, $J_\lambda$, and $C_\lambda$ gene content was found to be identical to that of the original L1 YAC as above.

Production of YAC Comprising Complete λ Light Chain Locus

A YAC containing the complete human germline immunoglobulin-λ light chain locus was generated by mating the 6-23 strain with a yeast clone comprising the L1 YAC containing HPRT and bcl-a, as described above. The yeast cells were plated on SC-HIS-LYS-ADE to eliminate haploids, and clones were picked and analysed by PFGE and Southern blot analysis as described above in Example 1. The analyses revealed that both YACs were present and confirmed that all λ gene elements were present. To induce meiosis for the generation of a YAC comprising the complete human immunoglobulin-λ light chain locus, the diploids grown on sporulation plates and then transferred to SC–ADE–LYS+CYH+ CAN plates. See Birren et al., supra, Vol. 3, pg. 495.

Clones were picked and analyzed by PFGE and Southern blot analysis as described above in Example 1. A YAC containing the entire human λ light chain locus in the germline configuration was identified and was designated yL. When 20 clones were grown in rich media (YPDA) and in selection media (SC–ADE–LYS), no instability was observed.

EXAMPLE 3

Production of Mice Bearing a Heritable Human Immunoglobulin-λ Light Chain Locus

Spheroplasts of the yeast clones were produced using Zymolyase 20T (1.5 mg ml-1) and then fused with 3B1 ES cells to create ES/yeast cell fusions (ESY) as described, e.g., by Jakobovits et al., Nature 362: 255-8 (1993), and WO98/24893, both of which are herein incorporated by reference. Cells were selected with HAT medium beginning 48 hours after fusion. Clones were picked and expanded. The ES cell lines were then analyzed by Southern blot for the presence and integrity of the human Ig λ YAC, using probes spanning the YAC created in Example 2 above.

Seven ES cell lines were found to contain the human Ig λ YAC intact. Positive ESY cell clones were expanded and microinjected into appropriate mouse blastocysts, e.g., C57BL/6J, using techniques well known in the art. Microinjected blastocysts were placed into the uterus of pseudopregnant C57BL/6 foster mothers. Chimeric animals were identified by coat color. Chimeric mice were mated to C57B6 females. Germline transmission of the ES cell genome was detected by coat color of the resulting progeny. Pups of agouti coat color were indicative of germline transmission of the ES cell genome, while pups of a black coat color have not been transmitted the ES cell genome.

Agouti-colored progeny of the chimeric mice were analyzed for the presence of the human Ig λ YAC in their genomes. A tail biopsy was taken from the agouti pups, the DNA was recovered using standard techniques, and the resulting DNA was analyzed by PCR for the presence of human Ig λ DNA. Transgenic pups are analyzed for the possession and integrity of an intact human Ig λ transgene by Southern blot analysis using probes outlined in Example 1.

EXAMPLE 4

Production of Transgenic Mice Comprising Human Immunoglobulin Heavy Chain and κ and λ Light Chain Genes To create transgenic mice comprising human immunoglobulin heavy, κ light, and λ light chain genes as well as substantially inactivated endogenous immunoglobulin heavy and light chain genes, the transgenic mice created by the methods described in Example 3 were mated with mice comprising human immunoglobulin heavy chain genes and κ light chain genes, and having substantially inactivated endogenous immunoglobulin heavy and light chains genes. Mice that may be used include the XenoMouse I strain (see, e.g., Green et al., Nature Genetics 7:13-21, 1994 and WO 98/24893), the L6 strain (see, e.g., WO 98/24893), the XenoMouse IIa strain (see, e.g., WO 98/24893) and mice comprising a non-cognate switch region (see, e.g., WO 00/76310), all of which are incorporated by reference. See also U.S. Pat. Nos. 5,939,598 and 6,162,963, both of which are herein incorporated by reference. Mice of the $F_1$ generation comprised a litter of mixed genotypes. Further matings were performed to attain the desired genotype. The transgenic mice comprising human immunoglobulin heavy, κ light, and λ light chain genes have been designated XenoMouse-KL. The transgenic mice comprising human immunoglobulin heavy and λ light chain genes have been designated XenoMouse-L.

Alternatively, spheroplasts bearing the YAC created in Example 2 above are fused with ES cells derived from mice comprising human immunoglobulin heavy chain and κ light chain genes and/or substantially inactivated endogenous immunoglobulin heavy and light chain genes. These ES cells may be derived from the XenoMouse® strains or the DI strain (see, e.g., U.S. Pat. Nos. 5,939,598 and 6,162,963 and WO 98/24893, herein incorporated by reference). The resultant ESY cells are then injected into blastocysts, implanted into pseudopregnant mice, and brought to term as described in Example 3.

EXAMPLE 5

Production of Transgenic Mice Comprising Human Immunoglobulin Heavy Chain and λ Light Chain Genes In another embodiment, transgenic mice comprising human immunoglobulin heavy chain and λ light chain genes, an intact mouse κ or λ chain gene, and substantially inactivated endogenous immunoglobulin heavy and κ or λ light chain genes are made. The transgenic mice created by the methods described in Example 3 are mated with mice comprising human immunoglobulin heavy chain genes and substantially inactivated endogenous immunoglobulin heavy chain genes. These mice are described in, e.g., U.S. Pat. Nos. 5,939,598 and 6,162,963. Mice of the $F_1$ generation will comprise a litter of mixed genotypes. Further matings can be performed to attain the desired genotype.

Alternatively, spheroplasts bearing the YAC created in Example 2 above are fused with ES cells derived from mice comprising human immunoglobulin heavy chain genes as well as substantially inactivated endogenous immunoglobulin heavy chain and κ or λ light chain genes. The resultant ESY cells are then injected into blastocysts, implanted into pseudopregnant mice, and brought to term as described in Example 3.

EXAMPLE 6

B-cell Development and Human Antibody Production by XenoMouse-KL Mice

To further characterize XenoMouse-KL transgenic mice, peripheral blood and spleen lymphocytes are isolated from 8-10 week old mice and controls. The cells are purified on Lympholyte M (Accurate) (San Diego, Calif.) and treated with purified anti-mouse CD32/CD 16 Fc receptor (Pharmingen, #553142) (San Diego, Calif.) to block non-specific binding to Fc receptors. Next, the cells are stained with various antibodies and analyzed on a FACS Vantage (Becton Dickinson, CELLQuest software). The panel of antibodies that are used to stain XenoMouse-KL cells include: Cy-5 labeled rat anti-mouse CD19 (Caltag, #RM7706); FITC-labeled anti-human IgM (Pharmingen, #555782);PE-labeled anti-human IgM (PharMingen #34155X); FITC-labeled anti-human Igλ (PharMingen #555796); PE-labeled anti-human Igκ (PharMingen #555792) FITC-labeled anti-mouse Igλ (Pharmingen, #553434.

For staining control wild-type 129xB6 mice, the antibodies used included Cy-5 labeled rat anti-mouse CD19 (Caltag, #RM7706); FITC-labeled antimouse IgM (PharMingen #553408); FITC-anti-mouse κ (PharMingen #550003); PE-anti-mouse IgM (PharMingen #553409); PE-anti-mouse κ (PharMingen #559940).

Lymphocytes from spleen and lymph nodes of one to four animals from XenoMouse G1 and XenoMouse G2 strains making both human λ and κ chains were evaluated and compared to XenoMouse G2 and XenoMouse G1 making only κ chains and wild type B6/129 mice using flow cytometry. The XenoMouse strains making both human λ and κ chains were XMG2-KL and XMG1-KL, making human IgG2 and human IgG1, respectively. The XMG2-KL and XMG1-KL mice showed efficient reconstitution in the B-cell compartment and substantial expression of human Ig λ chains. As observed in the human, the expression of human Igκ dominates over human Igλ. In the XenoMouse strains expressing both human Igκ and human Igλ, the ratio of human Igκ to human Igλ was approximately 60:40, as seen in humans. Thus, transgenic mice comprising comprising human immunoglobulin heavy, κ light, and λ light chain genes show significant human antibody and immune system development.

EXAMPLE 7

Serum Levels of Human Antibodies in Unimmunized Mice

An ELISA for determination of human antibodies in unimmunized mouse serum is carried out. For more detailed information and procedures on immunoassays see E. Harlow et al., Antibodies: A Laboratory Manual, Chapter 14, "Immunoassay", pages 553-614, Cold Spring Harbor Laboratory Press, Cold Spring Harbor, N.Y. (1988), herein incorporated by reference.

The concentration of human immunoglobulins is determined using the following capture antibodies: goat anti-human IgG (Caltag, H10500), goat anti-human Igκ (Southern Biotechnology, 2060-01), goat anti-human IgM (Southern Biotechnology, 2020-01), goat anti-human Igλ (Caltag, H16500) for human γ, κ, μ and λ Ig, respectively, and goat anti-mouse λ (Southern Biotechnology, 1060-01) to capture mouse λ Ig.

The detection antibodies used in ELISA experiments were goat anti-mouse Igλ-horseradish peroxidase (HRP) (Caltag, M-33607), goat anti-human IgG-HRP (Caltag, H10507), mouse anti-human IgM-HRP (Southern Biotechnology, 9020-05), goat anti-human κ-HRP (Southern Biotechnology, 2060-05), goat anti-human Igλ-HRP (Southern Biotechnology, 2070-05). Standards used for quantitation of human and mouse Ig were: human $IgG_2$ (Abgenix, hIgG2), human $IgG_2κ$ (Abgenix, hIgG2/k), human $IgG_2λ$ (Sigma, 1-4264), human IgMκ (Caltag, 13000), human IgMλ (Caltag, 13200) and mouse $IgG_{2a}λ$ (Sigma, M-6034).

Significant expression of human Igλ chains were detected in the serum of XenoMouse G1 and XenoMouse G2 making both human Igκ and human Igλ. Fully human IgG2λ and IgG1λ antibodies were detected. See FIG. 5.

EXAMPLE 8

Production of Human Monoclonal Antibodies

Immunization and Hybridoma Generation

Groups of four 6-week old XenoMice G2-κ/λ were immunized subcutaneously in the footpad with 10 μg of either recombinant human MCP-1 or $10^7$ human CEM cells. Groups of four 6-week old XenoMice G1-κ/λ were immunized subcutaneously in the footpad with 10 μg of recombinant MN-Fc. The antigen was emulsified in Titermax Gold (Sigma; cat. # T2684) for the primary immunization and in alum (aluminum phosphate gel adjuvant; Superfos Biosector a/s, distributed by E.M. Sargent Pulp and Chemical Co., Clifton, N.J., cat #1452-250) for the additional immunizations following conventional techniques, such as those described in Harlow et al., supra, pages 53-138, herein incorporated by reference. Immunizations were carried out two times per week for three weeks for at least 5 booster immunizations (boosts).

The mice receive a final injection of antigen or cells in phosphate-buffered saline (PBS) four days prior to fusion of the lymphocytes from the draining lymph nodes and myeloma cells. Isolation of the spleen lymphocyte cells and subsequent fusion is carried out following conventional techniques, such as those described in Harlow et al., supra, pages 139-244, herein incorporated by reference.

Alternatively, elcetrocell fusion may be carried out. Lymph node lymphocytes were prepared for electrocell fusion by first enriching for B cells through depletion of T-cells using a magnetic column. 0.9 ml of DMEM (Dulbecco's Modified Eagle's Medium, JRH Biosciences, cat. #51444-79P, plus 4500 mg/L glucose, 110 mg/L sodium pyruvate, no L-Glutamine) was added per 100 million lymphocytes to the cell pellet. The cells were resuspended gently but completely. 100 μl of CD90+ magnetic beads (Mouse CD90+ magnetic beads, Miltenyi Biotech, cat. #491-01) were added per 100 million cells, and mixed gently and well. The cells were incubated with the magnetic beads at 4° C. for 15 minutes. During the incubation, the magnetic column was pre-washed with 3 ml of DMEM. After the 15-min incubation, the magnetically-labeled cell suspension containing up to $10^8$ positive cells (or up to $2×10^9$ total cells) was pipetted onto the LS+ column (Miltenyi Biotech, cat. #424-01). The cell suspension was allowed to run through and the effluent collected as the CD90-negative fraction. The column was washed with 3×3 ml of DMEM and the total effluent collected as the CD90-negative fraction (most of these cells were B cells).

Lymphocytes enriched for B cells were fused by electrocell fusion with the P3-X63-Ag8.653 myeloma and were subjected to hypoxanthine/azaserine (HA) (Sigma, cat. #A9666) selection. For electrocell fusions, myeloma cells were harvested by centrifugation in a sterile centrifuge tube (either a 50 ml or a 250 ml tube, based on the number of cells harvested), and resuspended in DMEM. Myeloma cells and B cells were combined in a 1:1 ratio and mixed well in a 50 ml-conical tube. Cells were pelleted via centrifugation. 2-4 ml of Pronase solution (CalBiochem, cat. #53702; 0.5 mg/ml in PBS) was added and the cell pellet resuspended gently. The enzyme treatment proceeded for no more than 2 minutes and the reaction was stopped by adding 3-5 ml of fetal bovine serum. Electrocell fusion (ECF) solution (0.3M Sucrose, (Sigma, Cat. #S7903), 0.1 mM Magnesium Acetate (Sigma, Cat #M2545), 0.1 mM Calcium Acetate (Sigma, Cat #C4705), sterile filtered with 0.22 micron filter) was added to make 40 ml total volume and the cells pelleted by centrifugation. The supernatant was removed and the cells resuspened gently in a small volume of ECF solution then more ECF solution was added to a 40 ml total volume. The cells were mixed, counted and pelleted by centrifugation. The cell pellet was resuspened in a small volume of ECF solution to adjust the concentration to $2×10^6$ cells/ml.

The electrocell generator was Model ECM2001, Genetronic, Inc., (San Diego, Calif.). A 2 ml electrocell fusion chamber system was used for fusions. Electrocell fusion conditions were:

Alignment condition: voltage=50V, time=50 sec
Membrane breaking: voltage=3000V, time=30 microsecs
Post-fusion holding time: 3 sec After electrocell fusion, the cell suspension was removed carefully under sterile conditions from the fusion chamber and transfered into a sterile tube containing the same volume (or more) of hybridoma medium and incubated for 15-30 minutes in a 37° C. incubator. Cells were pelleted by centrifugation. Cells were resuspeneded in small volume of ½ strength HA medium gently and thoroughly and adjusted to appropriate volume with ½ HA medium so as to plate 5×10$^6$ B cells per 96-well plate and a volume of 200 μl per well. Cells were pipetted into 96-well plates. On day 7 or 10, 100 μl of medium is removed from each well and replaced with with 100 μl of ½ HA medium. Alternatively, lymphocytes can be fused to myeloma cells via polyethylene glycol fusion and subjected to HAT selection as previously described [G. Galfre, et al., Methods Enzymol. 73:3-46 (1981)].

After 10-14 days of culture, hybridoma supernatants were screened for antigen-specific IgG2κ, IgG2λ monoclonal antibodies. Briefly, ELISA plates (Fisher, Cat. No. 12-565-136) were coated with 50 μl/well of CD147-Fc (2 ug/ml, for CEM group), MCP-1 (2 ug/ml) and MN-his (2 μg/ml) in Coating Buffer (0.1 M Carbonate Buffer, pH 9.6, NaHCO$_3$) and incubated at 4° C. overnight. After incubation, the plates were washed with Washing Buffer (0.05% Tween 20 in PBS) 3 times. To each well was added 200 μl//well Blocking Buffer (0.5% BSA, 0.1% Tween 20, 0.01% Thimerosal in 1× PBS) and incubated at room temperature for 1 hour. After incubation, the plate was washed with Washing buffer 3 times. Then, to each plate was added 50 μl/well of hybridoma culture supernatants, positive, negative controls and incubated at room temperature for 2 hours. After incubation, the plate was washed with Washing Buffer 3 times. Then, to each plate was added 100 μl/well of detection antibody GT anti-huIgGfc-HRP (Caltag, Cat. #H10507), and incubated at room temperature for 1 hour. After incubation, the plates were washed with Washing buffer 3 times. Then to each plate was added 100 μl/well developing solution (10 ml Substrate Buffer, 1 mg OPD (o-phenylaedediamine, Sigma Cat No. P-7288), 10 μl 30% H$_2$O$_2$ (Sigma)), making the solution fresh before use. The reaction was allowed to develop about 10 minutes (until control wells barely start to show color), then 50 μl/well stop solution (2 M H$_2$SO$_4$) was added. The OD values were read on an ELISA plate reader at wavelength 492 nm.

For secondary screens, to determine Ig light chain usage, 3 sets of samples representing the positive wells in first screening were screened, one set for hIgHG detection, one set for hK detection and one set for hΛ detection. The detecting antibodies were GT anti-hIgK-HRP (Southern Biotechnology, Cat. #2060-05) and GT anti-hIgλ (Southern Biotechnology, Cat. #2070-05) in secondary screening.

XenoMouse-KL strains produced fully human IgGλ monoclonal antibodies. For the immunogens, CEM cells and MCP-1 protein, both fully-human IgG2κ and IgG1λ antigen-specific monoclonal antibodies were obtained from the XenoMouse G2-KL mice. For the recombinant MN-FC fusion protein, one mAb, afully human IgG1λ, was obtained from the XenoMouse G1-KL mice.

EXAMPLE 9

Characterization of Human Light Chain λ YAC Integration

Genomic DNA was prepared from ES and 3B 1 cell lines by phenol/chloroform extraction according to the method of Gross-Bellard et al. (Gross-Bellard, M., Oudet, P., and Chambon, P., Isolation of high molecular weight DNA from mammalian cells Eur. J. Biochem. 36: 32-38, 1973). Genomic DNA from XenoMouse strains was extracted from tail clips using QIAGEN DNeasy 96 tissue kit (Qiagen Cat. No. 69582). 10 μg of each sample was digested with EcoRI (for hybridization with Vλ probes), PvuII and PstI (for Cλ probes), and SacI (for λ 3' enhancer probes). The digested DNA samples were run on 0.7% agarose gel (SEAKEM ME, FMC) in 0.5× Tris/borate/EDTA (TBE) buffer, for 16 hours. DNA was transferred to a GENESCREEN (NEN Life Science) nylon membrane by standard alkaline transfer. DNA probes, described below, were radiolabeled using High Prime kit (Roche Cat. No. 1 585 592). Hybridization was performed at 65° C. for 1 hour. Low stringency washes were performed at 65° C. using 1×SSC, 0.1% SDS solution for 1 hour. Two high stringency washes were performed in 0.1×SSC, 0.1% SDS at 65° C. The washed membranes were exposed at −70° C. to X-ray film (Eastman Kodak, Rochester, N.Y.) backed by an intensifying screen.

The Vλ family-specific probes used to detect human Vλ genes were Vλ2a2, Vλ3P, Vλ5c, Vλ7a, and Vλ8a, Cλ and λ 3' enhancer. The Vλ and Cλ probes have been described previously (Prippiat et al., Organization of the human immunoglobulin λ light-chain locus on chromosome 22q11.2. Hum. Mol. Genet. 4, 983-991, 1995; Udey, J. A. and Blomberg, B., Human λ light chain locus: Organization and DNA sequences of three genomic J regions. Immunogenetics 25:63). The 450 bp λ 3' enhancer probe was amplified from human genomic DNA, using forward primer 5'-GATAAGAGTCCCTC-CCCACA-3' (SEQ ID NO: 16) and reverse primer 5'-GGC-CATGAGCTCAGTTTCTC-3' (SEQ ID NO: 17).

The organization of the human immunoglobulin lambda light chain locus in XenoMouse was determined by Southern blot hybridization. The integrity of the Vλ and Cλ in XenoMouse was determined by Southern blot hybridization of EcoRI-digested DNA, hybridized with several different Vλ or Cλ family-specific segments located within five gene-rich clusters. See FIGS. 6A-G. The presence of the λ 3' enhancer region was also determined (data not shown). The hybridization patterns of all Vλ and Cλ probes were compared to that of human genomic DNA and to that of the λ YAC. The Southern blot analyses revealed that each of the Vλ genes identified in human genomic DNA is present in the λ YAC integrated in ES cells and in genomic DNA extracted from tails of three XenoMouse strains.

Specifically, human genomic DNA, genomic DNA extracted from XenoMouse strains G43C1L3, G2 XMG2L3 and G1 3B3L3, and genomic DNA extracted from ES cell line V8.5A was extracted and digested with EcoRI (FIGS. 6A-D), with PstI (FIG. 6E) or PvuII (FIG. 6F) as described above. As a positive control, 1 μg of λ YAC was added to 10 μg of the genomic DNA of 3B1, which is a mouse that does not contain the human λ locus, and digested with the same enzymes. As a negative control, 10 μg of the genomic DNA of 3B1 was digested with the same enzymes. These samples were subjected to Southern blot analysis as described above. The probes used were as follows: for Vλ2, Vλ2a2 probe (FIG. 6A); for Vλ3, the Vλ3p probe (FIG. 6B); for Vλ5, the Vλ5C probe (FIG. 6C); for Vλ7, the Vλ7a probe (FIG. 6D); for Vλ8, the Vλ8a probe (FIG. 6E); and for Cλ, the Cλ probes described above. Southern blot analysis of the EcoRI-, PstI- or PvuII-digested DNA showed a uniform pattern of hybridization bands for all analyzed samples. See FIGS. 6A-G. The presence of identical hybridization bands for the Vλ, Cλ and the λ 3' enhancer confirmed that the λ YAC integrated in XenoMouse strains spans the entire locus. In all three XenoMouse strains tested, the λ YAC was transmitted with no apparent deletions or rearrangements. Further, the hybridization pattern using Vλ3 probe detects the largest VλIII family, which is composed of ten functional V segments and 13 pseudogenes. Thus, Southern blot analysis indicates that 1 Mb of the entire gene locus of HuIgλ YAC contains Vλ genes, seven paired Jλ-Cλ segments, and the 3'λ enhancer in the correct germline configuration.

EXAMPLE 10

Igλ Usage in Antibody Response

XenoMice KL were immunized with various antigens. Antibodies that were produced by the XenoMice were characterized to determine which antibodies had a κ light chain and which had a λ light chain. The ratio of κ light chain to λ light chain in the various antibodies produced was expected to be approximately 60:40 in the antibodies produced produced by the XenoMice because approximately 40% of antibodies comprise λ light chains and 60% of antibodies comprise κ light chains in humans. Surprisingly, for some antigens and XenoMice strains, Igλ dominated some immune responses. See Table 3 (Igλ dominant responses are in bold).

TABLE 3

|         | κ:λ (%) |       |      |
|---------|---------|-------|------|
| Ag (kD) | XMG1    | XMG2  | XMG4 |
| 8       | 50:50   | 60:40 | —    |
| 17.2    | 60:40   | 40:60 | —    |

TABLE 3-continued

|         | κ:λ (%) |       |      |
|---------|---------|-------|------|
| Ag (kD) | XMG1    | XMG2  | XMG4 |
| 17      | 60:40   | 60:40 | 50:50 |
| 9       | —       | 30:70 | 20:80 |
| 104     | —       | 60:40 | 50:50 |
| 2       | 20:80 | 50:50 | 50:50 |
| 26      | 30:70 | —   | 30:70 |
| KLH     | 90:10   | 90:10 | —    |

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

We claim:

1. A transgenic mouse whose genome comprises a substantially complete human λ light chain locus comprising V, J, and constant region genes, wherein the mouse comprises YAC yL.

2. The transgenic mouse according to claim 1, wherein said mouse further comprises a human immunoglobulin heavy chain locus comprising V, D, J, and constant region genes or a portion thereof, a human immunoglobulin κ light chain locus comprising V, J, and constant region genes or a portion thereof or both said human immunoglobulin heavy chain locus or portion thereof and said human immunoglobulin κ light chain locus or portion thereof.

3. A transgenic mouse whose genome comprises:
   a) a substantially inactivated endogenous heavy chain locus;
   b) a substantially inactivated endogenous κ light chain locus;
   c) a human heavy chain locus comprising V, D, J, and constant region genes;
   d) a human κ light chain locus comprising V, J, and constant region genes; and
   e) a substantially complete human λ light chain locus comprising V, J, and constant region genes,
wherein the mouse comprises YAC yL.

4. A method for producing a cell line that produces a human monoclonal antibody or a fragment thereof directed to an antigen, comprising:
   a) immunizing the transgenic mouse of claim 2 or 3 with said antigen;
   b) allowing said transgenic mouse to mount an immune response to said antigen;
   c) isolating B lymphocytes from said transgenic mouse;
   d) immortalizing said B lymphocytes;
   e) creating individual monoclonal populations of said immortalized B-lymphocytes; and
   f) screening said immortalized B lymphocytes to identify a cell line that produces an antibody directed to said antigen.

5. A cell line produced by the method according to claim 4.

6. The transgenic mouse of claim 1, comprising an active endogenous lambda light chain locus.

7. The transgenic mouse of claim 2, wherein the human immunoglobulin heavy chain locus is introduced by a YAC.

8. The transgenic mouse of claim 3, wherein the transgenic mouse expresses human Ig-kappa chains and human Ig-lambda chains in a ratio of 60:40.

9. A method for producing a B lymphocyte that produces a human monoclonal antibody or a fragment thereof directed to an antigen, comprising:
   a) immunizing the transgenic mouse of claim 2 or 3 with said antigen;
   b) allowing said transgenic mouse to mount an immune response to said antigen;
   c) isolating B lymphocytes from said transgenic mouse; and
   d) screening said B lymphocytes to identify a cell that produces an antibody directed to said antigen.

* * * * *